US008938111B2

(12) United States Patent
Kingston et al.

(10) Patent No.: US 8,938,111 B2
(45) Date of Patent: Jan. 20, 2015

(54) COMPUTED TOMOGRAPHY IMAGING PROCESS AND SYSTEM

(75) Inventors: Andrew Maurice Kingston, Griffith (AU); Adrian Paul Sheppard, Fisher (AU); Trond Karsten Varslot, Bruce (AU); Shane Jamie Latham, Mawson (AU); Arthur Sakellariou, Doncaster (AU)

(73) Assignee: FEI Company, Hillsboro, OR (US)

(*) Notice: Subject to any disclaimer, the term of this patent is extended or adjusted under 35 U.S.C. 154(b) by 122 days.

(21) Appl. No.: 13/519,516

(22) PCT Filed: Jan. 13, 2011

(86) PCT No.: PCT/AU2011/000038
§ 371 (c)(1),
(2), (4) Date: Jun. 27, 2012

(87) PCT Pub. No.: WO2011/085448
PCT Pub. Date: Jul. 21, 2011

(65) Prior Publication Data
US 2012/0301004 A1    Nov. 29, 2012

(30) Foreign Application Priority Data

Jan. 13, 2010  (AU) .................................. 2010900104

(51) Int. Cl.
  *G06K 9/00* (2006.01)
  *A61B 6/03* (2006.01)
  *A61B 6/00* (2006.01)
  *G06T 11/00* (2006.01)
  *G01N 23/04* (2006.01)
  *A61B 6/02* (2006.01)

(52) U.S. Cl.
  CPC ............... *A61B 6/032* (2013.01); *A61B 6/5205* (2013.01); *A61B 6/582* (2013.01); *A61B 6/587* (2013.01); *G06T 11/005* (2013.01); *G01N 23/046* (2013.01); *A61B 6/027* (2013.01); *A61B 6/4085* (2013.01); *Y10S 128/922* (2013.01); *Y10S 128/923* (2013.01)
  USPC ........... 382/131; 382/128; 382/132; 128/922; 128/923

(58) Field of Classification Search
  USPC .......... 382/128, 131, 132, 284, 294; 128/922, 128/923
  See application file for complete search history.

(56) References Cited

U.S. PATENT DOCUMENTS

| 5,493,593 A | 2/1996 | Muller et al. |
| 6,917,668 B2* | 7/2005 | Griffith ......................... 378/163 |
| 7,012,986 B1* | 3/2006 | Chao et al. ...................... 378/4 |
| 7,088,099 B2* | 8/2006 | Doddrell et al. .............. 324/309 |

(Continued)

OTHER PUBLICATIONS

Supplementary European Search Report, EP 11 73 2584, completed Aug. 12, 2013.

(Continued)

Primary Examiner — Yosef Kassa
(74) Attorney, Agent, or Firm — Hamilton, Brook, Smith & Reynolds, P.C.

(57) ABSTRACT

A computed tomography imaging process, including: accessing projection data representing two-dimensional projection images of an object acquired using a misaligned tomographic imaging apparatus; and processing the projection data to generate misalignment data representing one or more values that quantify respective misalignments of the tomographic imaging apparatus.

29 Claims, 20 Drawing Sheets

(56) References Cited

U.S. PATENT DOCUMENTS

| | | | |
|---|---|---|---|
| 7,333,648 B2* | 2/2008 | Edic et al. | 382/131 |
| 7,430,271 B2* | 9/2008 | Griffith | 378/24 |
| 7,573,973 B2 | 8/2009 | Tang et al. | |
| 7,606,345 B2* | 10/2009 | Nishide et al. | 378/4 |
| 7,835,561 B2* | 11/2010 | Meyer et al. | 382/131 |
| 8,611,630 B1* | 12/2013 | Katsevich et al. | 382/131 |
| 8,794,761 B2* | 8/2014 | Kobayashi | 351/206 |
| 8,804,127 B2* | 8/2014 | Shimoyama et al. | 356/479 |
| 8,804,912 B2* | 8/2014 | Akahori | 378/163 |
| 8,824,759 B2* | 9/2014 | Liu et al. | 382/131 |
| 2009/0196393 A1 | 8/2009 | Wang et al. | |

OTHER PUBLICATIONS

Kyriakou, Y., et al., "Simultaneous misalignment correction for approximate circular cone-beam computer tomography," *Phys. Med. Biol.* 53:6267-6289 ( Nov. 2008).

Muller, R.A. and Buffington, A., "Real-time correction of atmospherically degraded telescope images through image sharpening," *Journal of the Optical Society of America* 64(9):1200-1210 (Sep. 1974).

Sun, Y., et al., "Reduction of Artifacts Induced by Misaligned Geometry in Cone-Beam CT," IEEE Transactions on Biomedical Engineering 2007, vol. 54, No. 8, pp. 1461-1471.

International Search Report, PCT/AU2011/000038, date of mailing Mar. 18, 2011.

Bronnikov, A. V., "Virtual Alignment of X-Ray Cone-Beam Tomography System Using Two Calibration Aperture Measurements," *Opt. Eng.*, 38(2), 381-386 (1999).

Karolczak, M., et al., Implementation of a Cone-Beam Reconstruction Algorithm for the Single-Circle Source Orbit with Embedded Misalignment Correction Using Homogeneous Coordinates, *Med. Phys.*, 28 (10), 2050-2069 (2001).

Feldkamp, L., et al., "Practical Cone-Beam Algorithm," *J. Opt. Soc. Am.*, A(1):612-619 (1984).

Shih, L., "Autofocus Survey: A Comparison of Algorithms," *Digital Photography III*, vol. 6502 of Proc. SPIE-IS&T, pp. 65020B-1-65020B-11 (2007).

Groen, F., et al., "A Comparison of Different Focus Functions for Use in Autofocus Algorithms," *Cytometry* 6, 81-91 (1985).

Wang, G., et al., "A General Cone-Beam Reconstruction Algorithm," *IEEE Transactions in Medical Imaging*, 12:486-496 (1993).

Katsevich, A., "An Improved Exact Filtered Backprojection Algorithm for Spiral Computed Tomography," *Advances in Applied Mathematics*, 32(4):681-697 (2004).

\* cited by examiner

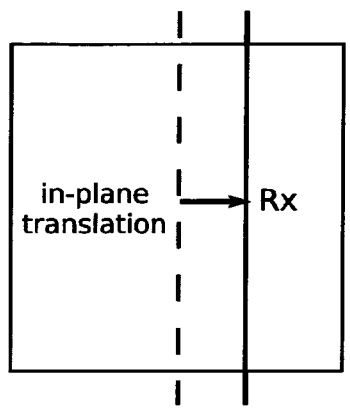
Figure 5A
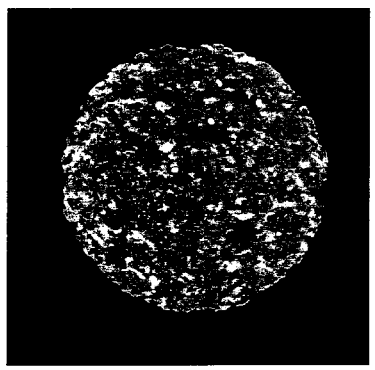 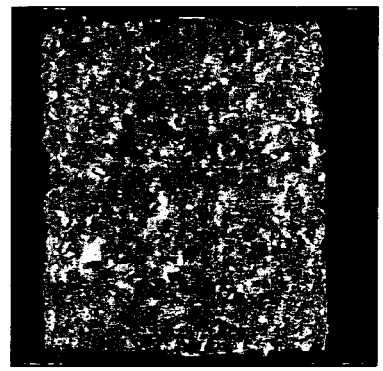
$R_X = 2_{PX}$
Figure 5B Figure 5C
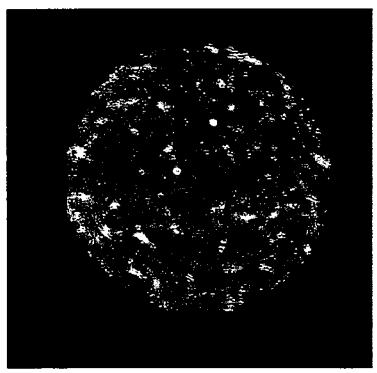 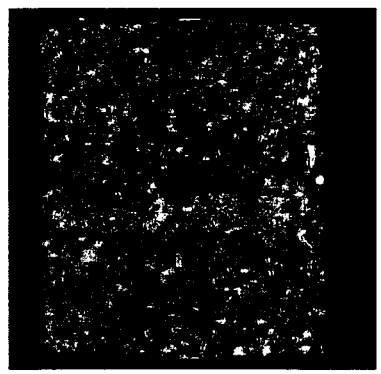
$R_X = 4_{PX}$
Figure 5D Figure 5E

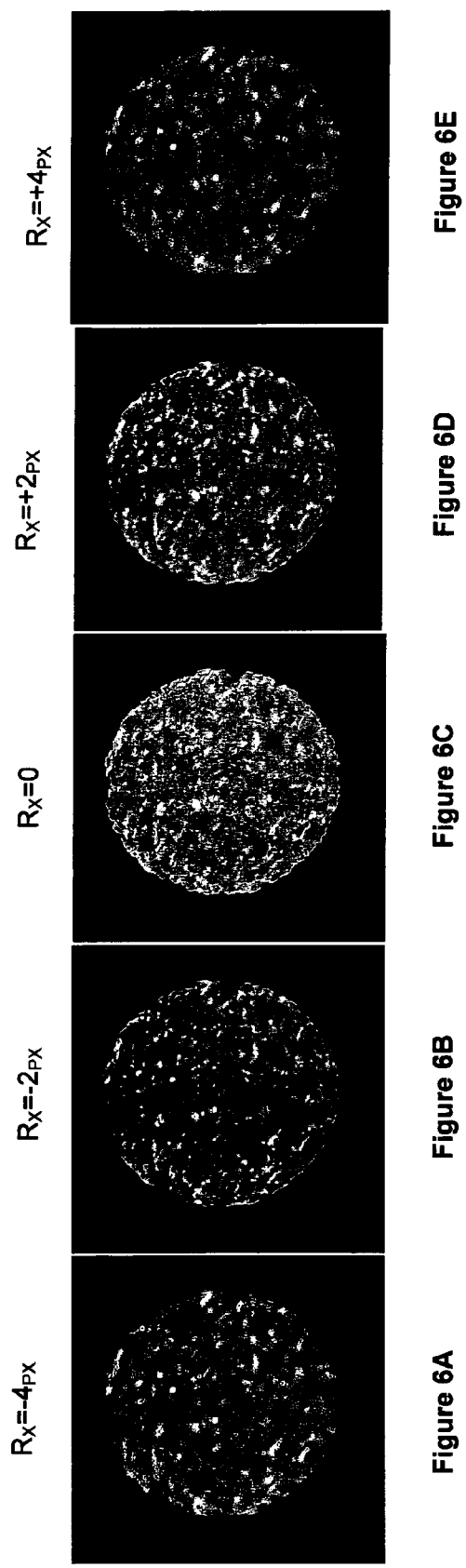

$R_\Phi = 2_{PX}$ $R_\Phi = 4_{PX}$

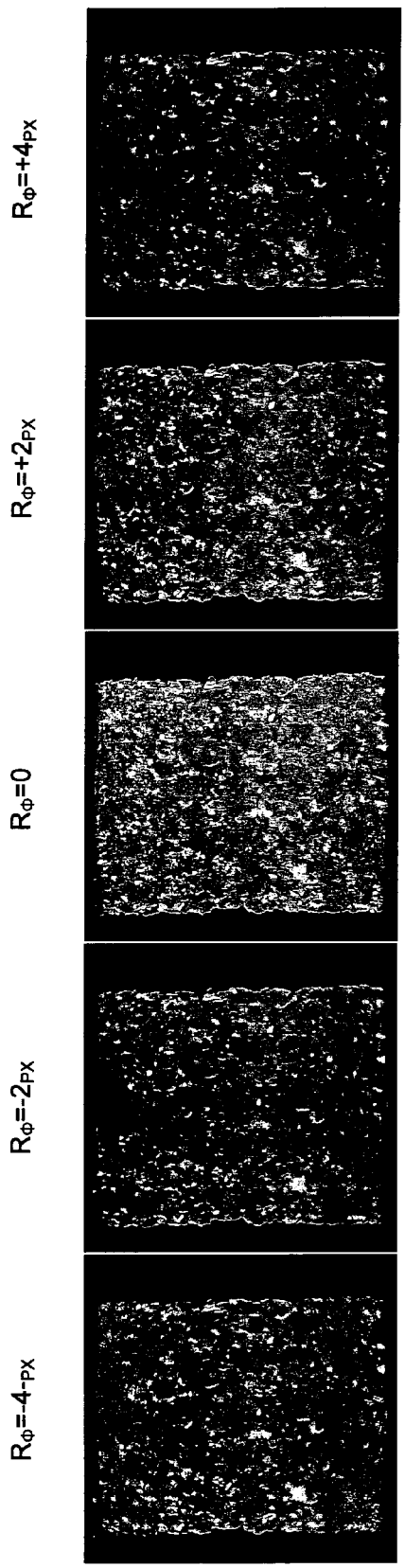

COMPUTED TOMOGRAPHY IMAGING PROCESS AND SYSTEM

This application is the U.S. National Stage of International Application No. PCT/AU2011/000038, filed Jan. 13, 2011, which designates the U.S., published in English, and claims priority under 35 U.S.C. §§119 or 365(c) to Australian Application No. 2010900104, filed Jan. 13, 2010.

TECHNICAL FIELD

The present invention relates to a computed tomography imaging process and system, and in particular to a computed tomography imaging process and system that correct or compensate for misalignments of a tomographic imaging apparatus or system.

BACKGROUND

The term computed tomography (CT) usually refers to processes whereby one or more images representing essentially any desired view of the internal structures of a physical object of interest are computed from a corresponding set of images representing respective geometric projections of the object.

To acquire the projection images of an object, a tomographic imaging apparatus requires (i) a source of particles or electromagnetic radiation to probe the object, (ii) a detector to measure the resultant probe-object interactions, and (iii) a means for changing the relative orientation between the source/detector components and the object. The projection images constituting the image set thus represent measurements of the probe-object interactions acquired at respective relative orientations between the source/detector components and the object. These directions are typically chosen such that the source and detector follow a particular trajectory relative to the object, the trajectory depending on the geometry between the source and the detector. Examples of such trajectories include circular, helical and saddle trajectories.

Once the set of two-dimensional projection images at respective different relative orientations has been generated, reconstruction algorithms are applied to these images to generate a corresponding data set referred to herein as a tomogram, representing the external and internal structural features of the object in three dimensions. Using the tomogram as input, display software can then be used to visualise the object in essentially any way desired by a user, including as a rotating semi-transparent object, static and dynamic slices through the object along arbitrary directions, and the like. Such 'reconstructed' images are referred to herein as tomographic images.

A particular difficulty with computed tomography is that the reconstruction algorithms assume that the three components of the tomographic imaging apparatus or system described above are in perfect mutual alignment. In practice this is rarely, if ever, the case, in particular, for imaging features with micrometer or nanometer dimensions. In such cases, the experiment is said to be 'misaligned', causing the reconstructed three-dimensional tomographic images to appear globally or locally "blurry" or "out-of-focus".

Various attempts have been made to overcome these difficulties. In A. V. Bronnikov, *Virtual Alignment of x-ray cone-beam tomography system using two calibration aperture measurements*, Opt. Eng. 38(2), 381-386 (1999), a specially manufactured calibration aperture is used in place of an actual object or sample of interest, and a cone-shaped x-ray beam is used to generate projection images of the aperture for opposite alignments of the aperture. These images are then processed to determine lateral and rotational misalignments of the rotational axis. Once measured in this manner, these misalignments can be used to modify projection images of actual samples of interest to compensate for the misalignments before applying standard reconstruction algorithms to the modified images.

Alternatively, the measured misalignments can be used as input to a modified reconstruction algorithm that corrects for some forms of misalignment, as described in M. Karolczak et. al., *Implementation of a cone-beam reconstruction algorithm for the single-circle source orbit with embedded misalignment correction using homogeneous coordinates*, Med. Phys. 28 (10), 2050-2069, 2001.

However, existing methods for correcting or compensating for misalignments of a tomographic apparatus are limited in their accuracy and applicability. It is desired, therefore, to provide a computed tomography imaging process and system that alleviate one or more difficulties of the prior art, or that at least provide a useful alternative.

SUMMARY

In accordance with the present invention, there is provided a computed tomography imaging process, including:
  accessing projection data representing two-dimensional projection images of an object acquired using a misaligned tomographic imaging apparatus; and
  processing the projection data to generate misalignment data representing one or more values that quantify respective misalignments of the tomographic imaging apparatus.

The process may include processing the projection data in accordance with the misalignment data to generate a tomogram of the object in which the one or more misalignments of the tomographic imaging apparatus have been substantially corrected.

The process may include processing the projection data in accordance with the misalignment data to generate modified projection data representing projection images of the object in which the one or more misalignments of the tomographic imaging apparatus have been substantially corrected.

The processing of the projection data may include:
  processing the projection data to generate trial reconstructed tomographic cross-sectional images for respective trial values of at least one misalignment of the tomographic imaging apparatus;
  processing the trial reconstructed tomographic images to generate respective evaluations of quality of the trial reconstructed tomographic images; and
  for each said at least one misalignment of the tomographic imaging apparatus, determining a corresponding value that best estimates the misalignment, based on the trial values and the corresponding evaluations of quality.

The trial reconstructed tomographic cross-sectional images may be generated by using fixed spatial positions and orientations for a source and rotation axis of the tomographic imaging apparatus and modifying the projection images to simulate the effect of changing the spatial position and/or orientation of a detector of the tomographic imaging apparatus.

The processing of the projection data may include processing the projection data to generate trial reconstructed tomographic cross-sectional images for each of a plurality of different slices of the corresponding tomogram.

The slices may represent orthogonal spatial orientations. The slices may represent all three orthogonal spatial orientations.

The projection data may be acquired along a scanning trajectory involving rotation of the object about a rotation axis, and the processing of the projection data may include processing the projection data to generate at least one trial reconstructed tomographic cross-sectional image that is not orthogonal to the rotation axis.

Each misalignment value may be determined by selecting one of the trial values of the misalignment that provides the best quality, or by interpolation based on the trial values and the corresponding evaluations of quality.

The values that best estimate each misalignment may be determined iteratively, with the iterations terminating when the values have been determined to an accuracy of less than 0.5 voxels.

The processing of the projection data may include evaluating the quality of reconstructed tomographic cross-section images generated on the basis of different combinations of values of said misalignments, and selecting one of said combinations based on said evaluations. The selected combination may be the combination that gives the highest quality reconstructed tomographic image.

The quality of reconstructed tomographic images may be evaluated using a measure of sharpness of the reconstructed tomographic images that depends on spatial information of the reconstructed tomographic images. Sharpness may be evaluated using the magnitudes of values in an image processed by a differentiation filter, or the magnitudes of high frequency transform coefficients generated by applying a transform function to the image.

The sharpness of each image may be calculated from the image directly and is distinct from image entropy which is an analysis of the image histogram only and thus ignores all spatial information of the image.

Misalignment value combinations may be chosen to maintain a constant magnification. Otherwise, changes in magnification can affect the determined sharpness measure without actually affecting the visual sharpness of the image.

An initial estimate for the misalignment may be obtained by scanning misalignment parameter space at a lower spatial resolution using down-sampled projection images. Progressively higher resolution images can then be used to refine the estimates until a final full-resolution estimate is obtained.

The two-dimensional projection images of the object may be acquired along a scanning trajectory produced by combining rotation and translation such that the two-dimensional projection images represent complete information about the object. The scanning trajectory may be helical or approximately helical.

The present invention also provides a computer-readable storage medium having stored thereon computer-executable programming instructions configured for execution of any one of the above processes.

The present invention also provides a computer-readable storage medium having stored thereon a computer program product configured for execution of any one of the above processes.

The present invention also provides a computed tomography imaging system configured to execute any one of the above processes.

The present invention also provides a computed tomography imaging system, including a data analysis component configured to:

receive projection data representing two-dimensional projection images of an object acquired using a misaligned tomographic imaging apparatus;

process the projection data to generate misalignment data representing one or more values that quantify respective misalignments of the tomographic imaging apparatus; and process the projection data in accordance with the misalignment data to generate modified projection data representing projection images of the object in which the one or more misalignments of the tomographic imaging apparatus have been substantially corrected.

BRIEF DESCRIPTION OF THE DRAWINGS

Embodiments of the present invention are hereinafter described, by way of example only, with reference to the accompanying drawings, wherein like reference numbers refer to like elements, and wherein:

FIG. 5A is a schematic illustration of the projection of a translationally misaligned rotational axis onto the detector plane of a tomographic imaging apparatus;

FIGS. 5B and 5C are reconstructed plan view and cross-sectional side view slices, respectively, of a tomogram of the core sample for the misaligned system of FIG. 5A, where the offset is 2 pixels;

FIGS. 5D and 5E are the same as FIGS. 5B and 5C, but for a translational offset of 4 pixels;

FIGS. 6A to 6E are a sequence of reconstructed plan view slices of a tomogram of the core sample for translational misalignments of the rotational axis of −4 px, −2 px, 0 px (i.e., aligned), +2 px, and +4 px, exemplifying the out-of-focus, to in-focus, back to out-of-focus sequence of images with respect to a translationally misaligned rotation axis;

FIGS. 8A to 8E are a sequence of reconstructed side-view slices of a tomogram of the core sample for rotational misalignments of the rotational axis of −4 px, −2 px, 0 px (i.e., aligned), +2 px, and +4 px, exemplifying the out-of-focus, to in-focus, back to out-of-focus sequence of images with respect to rotationally misaligned rotation axis;

DETAILED DESCRIPTION

Embodiments of the present invention are described below in the context of a tomographic imaging apparatus for micrometer-scale or nanometer-scale computed tomography of small objects, in particular cylindrical geological core samples, using a cone-shaped x-ray beam and a circular or helical scanning (sample) trajectory. However, it should be understood that the methods described herein are generally applicable to a wide range of different tomographic methods and apparatus, including both cone-beam and parallel beam systems, and are not limited to any particular apparatus type, beam type, object type, length scale, or scanning trajectory.

Figure 1:
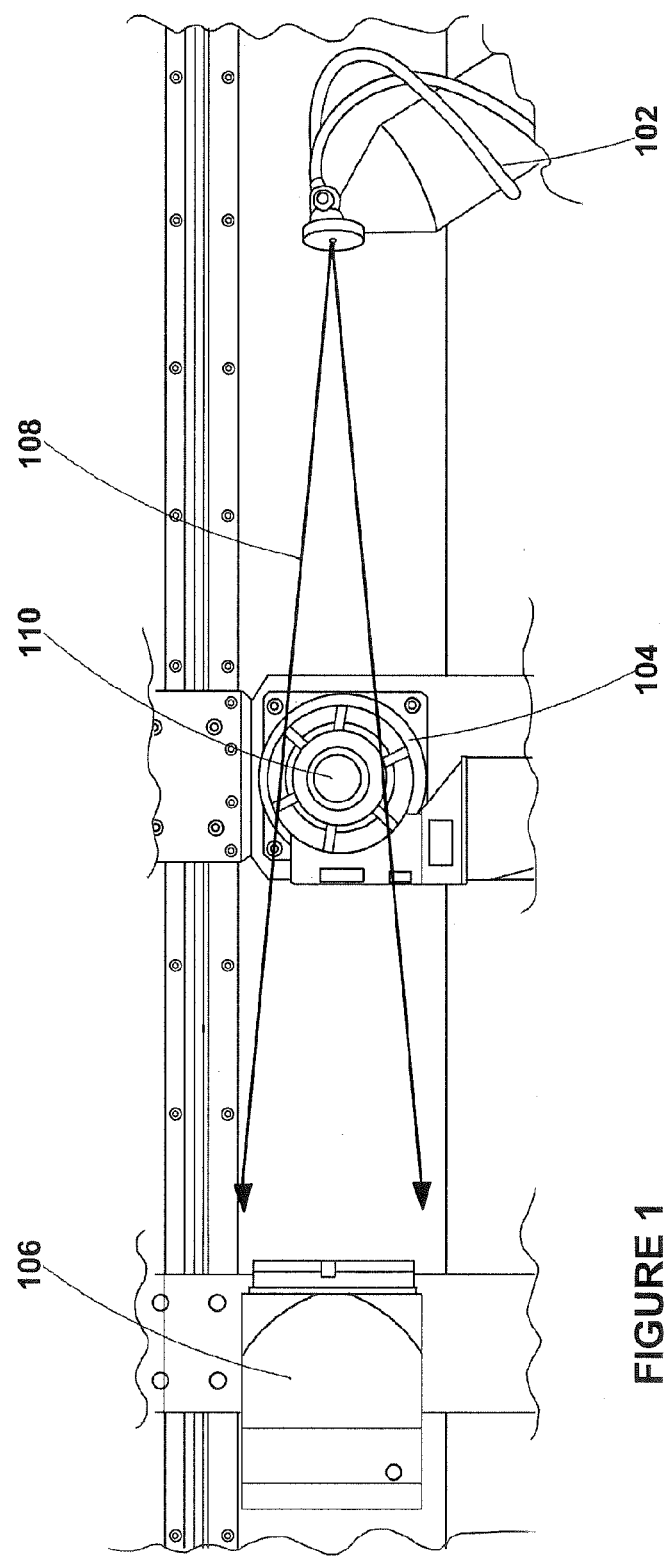
FIG. 1 is a plan view photograph of a tomographic imaging apparatus in which a cone-shaped x-ray beam generated by an x-ray source is transmitted through an object of interest to produce projection images on a detector.
Figure 17:
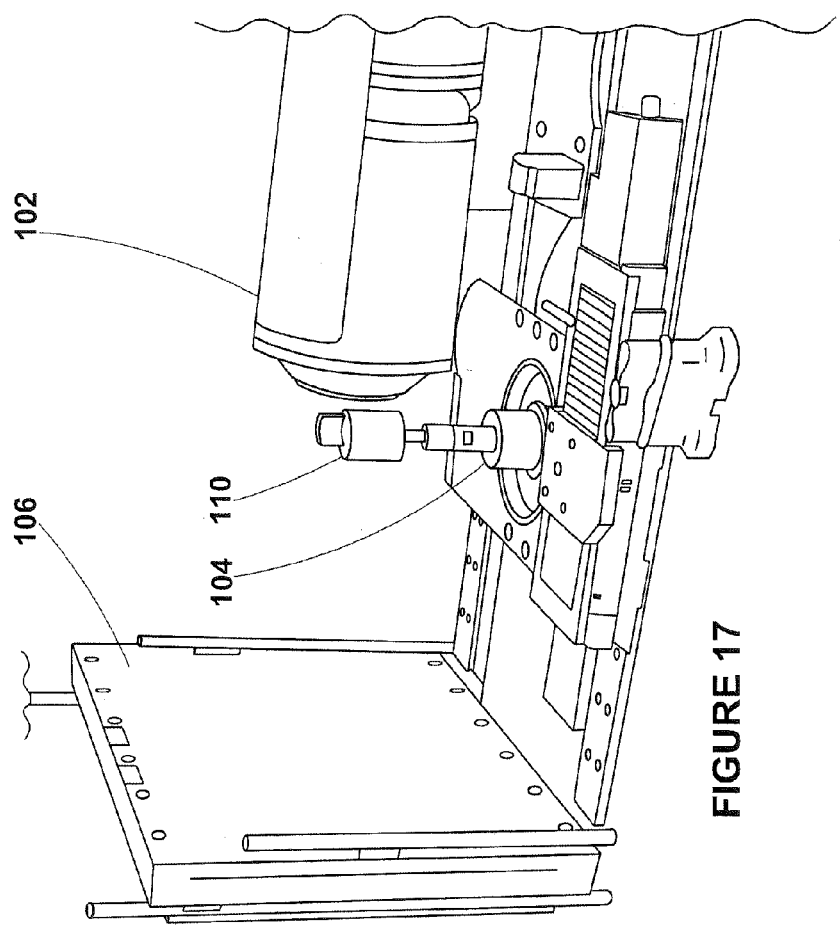
FIG. 17 is a photograph of a tomographic imaging apparatus in which the object of interest can be scanned along a helical scanning trajectory.

As shown in FIGS. 1 and 17, a computed tomography (CT) apparatus or system includes an x-ray source 102, a sample stage 104, and a detector 106. The x-ray source 102 generates a cone-shaped x-ray beam 108 that is transmitted through an object 110 mounted on the sample stage 104 to the detector 106. The cone angle and the fan angle are defined, respectively, as the vertical and horizontal half-angles subtended by the detector 106 at the source 102. The detector 106 includes a scintillator that generates visible light when irradiated by x-rays, and a CCD or amorphous silicon flat panel sensor mounted behind the scintillator that generates image data representing two-dimensional images of the spatial arrangement of scintillations generated by the scintillator, thus producing a two-dimensional image or map of x-ray intensity for the x-rays transmitted through the object. As will be appreciated, each of these images shows both external and internal structural features of the object, as projected along the directions of x-rays transmitted through the object to the detector 106. The image data generated by the detector 106 is acquired as a set of images stored in the form of binary data in a computer system (not shown) of the system for subsequent processing. The images are acquired sequentially, with the sample stage 104 being actuated to rotate the sample or object 110 by a small angle (and, in the case of helical scanning, to also translate the sample or object 110 by a small distance) between successive images, thus providing different geometric projections through the object. These steps are repeated until the sample has undergone a rotation of at least 180°+ fan angle and a complete set of projection images has been acquired. In the case of helical scanning, the steps are repeated until the sample or object 110 has undergone sufficient linear translation and rotation that complete information has been obtained for the region of interest of the sample.

The set of projection images is then processed using reconstruction software to generate a tomogram representing the three-dimensional external and internal structural features of the object. In the described embodiments, the standard Feldkamp-Davis-Kress (referred to hereinafter as "FDK") filtered back-projection method is one of the methods used for reconstruction, as described in L. Feldkamp, L. Davis, and J. Kress, *Practical cone-beam algorithm*, J. Opt. Soc. Am., A(1):612-619 (1984). The resulting tomogram can be displayed in the form of a partially transparent representation of the object that can be dynamically rotated and sliced in real-time by a user of the system to visualise and analyse the internal structural features of the object 110.

As described above, the reconstruction algorithms assume that the components of the apparatus directly involved in imaging the object, namely the source 102, sample stage 104, and detector 106 are all in perfect relative alignment. In practice, this is rarely, if ever, the case. In particular, for micro-CT and nano-CT systems, it may be impractical to achieve perfect alignment, with the result that the projection images are mutually misaligned, causing the reconstructed images of the object 110 to appear blurred or out of focus.

The tomographic imaging processes described herein process at least two projection images of an acquired set of projection images of an object of interest to automatically determine one or more values that quantify respective misalignments of the tomographic imaging apparatus used to generate the images. In the described embodiment, these values are then used to modify the set of projection images to effectively correct for those misalignments, thereby allowing standard reconstruction algorithms to be used to generate a tomogram or tomographic images that appear to be sharp or 'in focus'. However, it will be apparent to those skilled in the art that the determined values for misalignments of the system could alternatively be provided to a modified reconstruction algorithm that is capable of reconstructing according to the correspondingly modified geometry, thus avoiding the need to generate modified projection images.

The values for misalignments are determined by representing the misalignments by respective numeric parameters, and searching the parameter space to determine the combination of misalignment parameter values that provides the highest quality reconstructed tomographic images.

The quality of the reconstructed images is assessed using spatial information of those images, as opposed to statistical methods used in the prior art such as entropy. In the described embodiments, the particular spatial information used is sharpness, although other measures could in principle be used. The sharpness of the reconstructed images can be evaluated by any one of a range of different methods. However, sharper images generally have greater high spatial-frequency components, and thus sharpness can be estimated in the frequency domain using discrete Fourier, sine, cosine or wavelet transforms, or by differentiating the image, or by evaluating the depth of image peaks and valleys, or image contrast. In L. Shih, *Autofocus survey: a comparison of algorithms*, in *Digital Photography III*, Volume 6502 of Proc. SPIE-IS&T, pages 65020B-1-65020B-11, a range of DCT and image based methods were investigated over a variety of natural and artificial images and sharpness based on differentiation was found to be the most accurate and unimodal, (i.e., to produce a single maximum). From F. Groen, I. Young and G. Ligthart, *A comparison of different focus functions for use in autofocus algorithms*, Cytometry 6, 81-91, 1985, the general form of a differentiation based sharpness measurement is:

$$S\{f\} = \sum_x \sum_y (\max\{|\nabla^n f(x, y)| - T, 0\})^m$$

where the variable T sets a threshold on the image gradients contributing to the sharpness measure. In practice, at least for tomographic data obtained from the geological samples analysed to date, there does not seems to any significant effect on performance whether m and n are 1 or 2, and the threshold T seems to be unnecessary for these applications. The sharpness measure used by the tomographic imaging processes for these samples is thus the simplest and fastest, namely:

$$S\{f\} = \sum_x \sum_y |\nabla f(x, y)|^2.$$

Here, the squared gradient image, $|\nabla f|^2$, is determined as $G_h^2 + G_v^2$, where $G_h = g_h * f$, $G_v = g_v * f$, and $g_h$ and $g_v$ are any horizontal and vertical gradient masks, such as the Sobel masks:

$$g_h = \begin{matrix} -1 & 0 & 1 \\ -2 & x & 2 \\ -1 & 0 & 1 \end{matrix}, g_v = \begin{matrix} -1 & -2 & -1 \\ 0 & x & 0 \\ 1 & 2 & 1 \end{matrix}.$$

Using the above equations to evaluate image quality, the misalignments of the tomographic imaging apparatus can be determined by varying the values for the misalignment parameters and assessing their effects on the image quality. This search of misalignment parameter space can be performed using any of a wide variety of standard methods, including brute force searches and known multi-parameter optimisation/maximisation/minimisation methods, such as Powell's method.

Because the tomographic imaging processes described herein generate a reconstructed tomogram many times for different parameter values, they have the potential to require substantial computing resources. In the described embodiment, the efficiency of the process is improved in a number of ways, as follows.

Firstly, rather than reconstructing the entire 3D volume of the tomogram at each iteration, it is sufficient to reconstruct and analyse only a selection of 2D slices within the volume. Indeed, even a single slice can be sufficient as long as it is not oriented parallel to the horizontal plane (i.e., normal to the rotation axis). The most time consuming part of the reconstruction process is back-projection, which is $O(N^4)$ for an $N^3$ tomogram. By back-projecting only slices, the computation time of each step is reduced substantially. If M 2D slices are selected, then back-projection time is reduced to $O(MN^3)$. For example, if 3 slices of a $2048^3$ tomogram are selected for inspection, these are reconstructed approximately 700 times faster than the full 3D tomogram.

Secondly, it is desirable to minimise the number of parameter combinations for which to generate reconstructions at full spatial resolution. Accordingly, broad scans of parameter space are performed at lower spatial resolutions to find approximate parameter values, and these values are then used as seeds at a higher spatial resolution. Because the complexity of each iteration is $O(MN^3)$, each downscaling by a factor of 2 gives an 8 times speed up in generating the M reconstructed slices. This enables broad searches at coarse resolutions which are then improved with localised searches at subsequently higher resolutions. For the example above, if the 3 slices are reconstructed at $512^3$, these are generated approximately 44,000 times faster than the full tomogram.

Finally, an optimisation approach such as Powell's method can be employed to improve the efficiency of the process. This significantly reduces the number of reconstructions required, particularly when seeded with a reasonable estimate of the alignment parameters, (such as provided by a physical measurement before conducting an experiment). A multi-start task parallel process at a coarse resolution in parameter space quickly converges on the parameters, giving the global maximum. These parameters are then refined at subsequently higher resolutions using a data parallel process.

Circular Scanning

Figure 2:
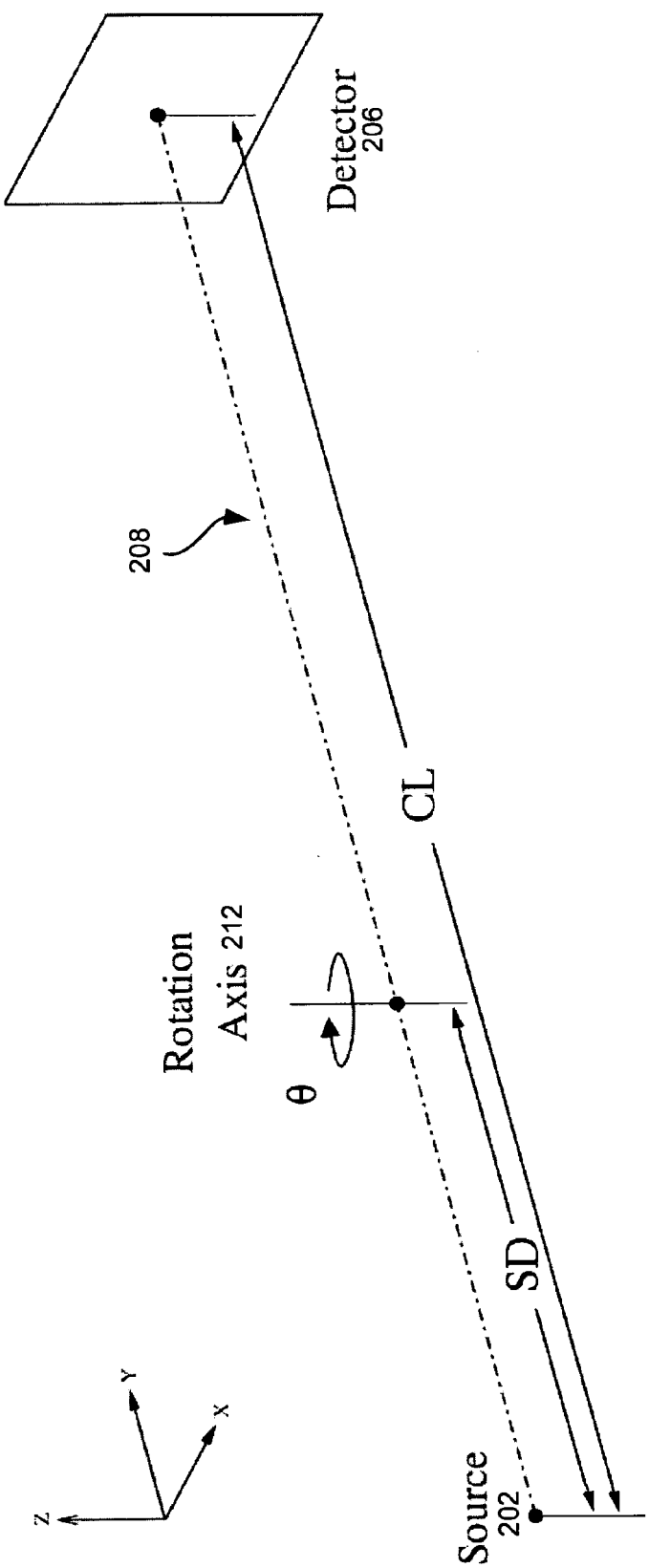
FIG. 2 is a schematic diagram illustrating the geometric parameters of a tomographic imaging apparatus such as the one shown in FIG. 1.

FIG. 2 is a schematic illustration of an arbitrary circular scanning tomographic imaging apparatus having three major components that are ideally in perfect mutual alignment.

First, there is a source 202 of electromagnetic radiation, a sample stage 204 having an axis of rotation 212, and a detector 206. Although some forms of tomographic imaging apparatus (e.g., those for imaging human beings) have the object (e.g., human) fixed and rotate the source 202 and detector 206 together as a unit, it will be understood by those skilled in the art that this is equivalent to the converse arrangement shown in FIG. 2. The (adjustable) distance between the source 202 and the rotation axis 212 is referred to as the sample distance SD, and the (adjustable) distance between the source 202 and the detector 206 is referred to as the camera length CL, with the resulting magnification for a diverging cone-shaped beam being given by CL/SD.

Figure 3C:
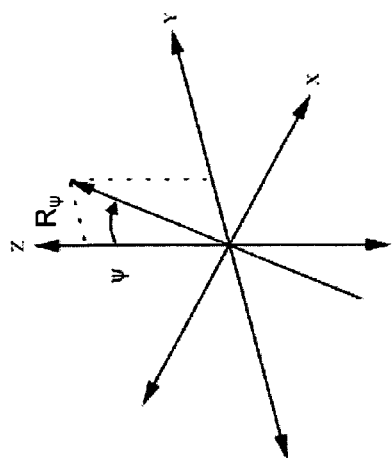
FIGS. 3A to 3C are schematic diagrams illustrating four forms of sample misalignment of a tomographic apparatus, namely two translation offsets of the sample rotation axis and two angular offsets of the sample.
Figure 3B:
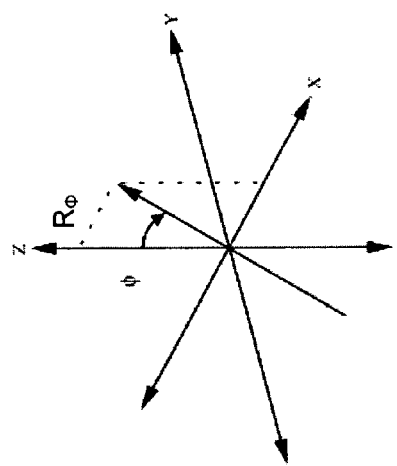
Figure 3A:
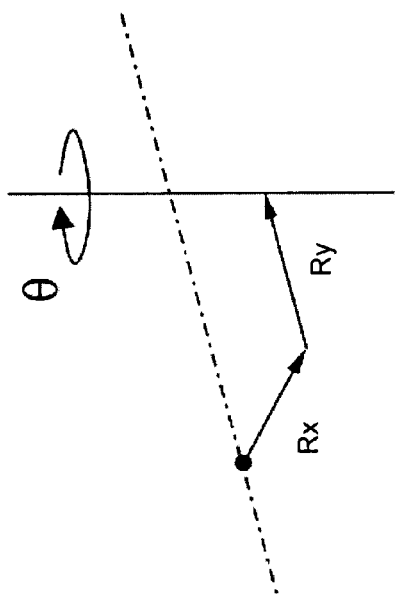

Any one or more of the source 202, rotation axis 212, and detector 206 can be misaligned, causing degradation in the quality of the reconstructed tomogram and hence the reconstructed tomographic images generated from the tomogram. Misalignments of the rotation axis 212 are particularly significant because they are magnified at the detector 206 by CL/SD. Misalignments of the rotation axis 212 are represented by four parameters. The first two parameters represent displacements or translation offsets of the rotation axis 212 from its ideal, aligned location. As shown in FIG. 3A, the parameter Rx represents a lateral or transverse displacement or offset of the rotation axis 212 from the ideal longitudinal axis 208 of the system, as shown in FIG. 2. The parameter Ry represents a longitudinal displacement or offset of the rotation axis 212 from the ideal location along the longitudinal axis 208, and consequently the parameter Ry is effectively an error in the sample distance SD, and consequently can also be represented as ASD.

Figure 4A:
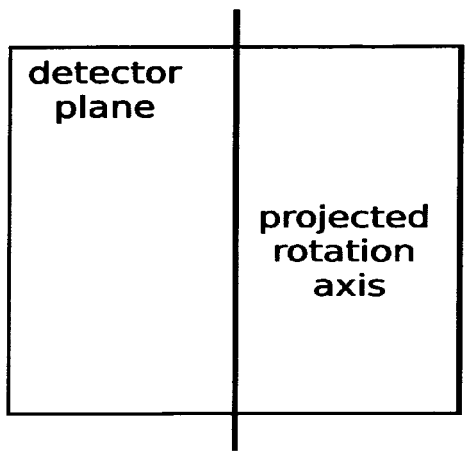
FIG. 4A is a schematic illustration of the projection of a perfectly aligned rotational axis onto the detector plane of the tomographic imaging apparatus of FIG. 1.
Figure 4B:
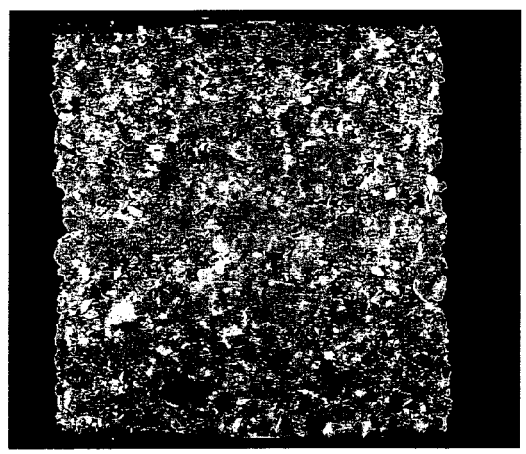
FIGS. 4B and 4C are reconstructed cross-sectional side view and plan view slices, respectively, of a tomogram of a cylindrical geological core sample for the perfectly aligned system of FIG. 4A.
Figure 4C:
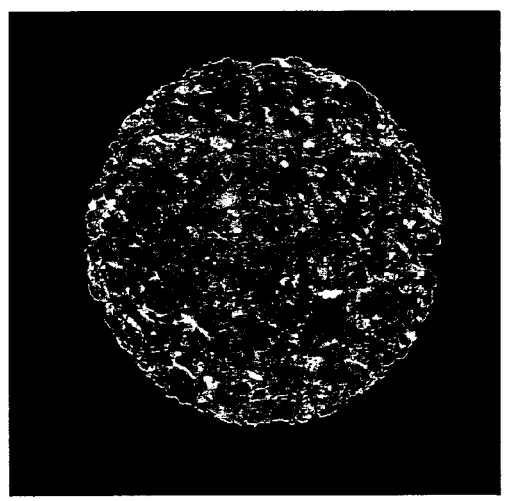

FIG. 4A is a schematic illustration of the projection of the rotational axis 212 onto the detector 206 where Rx=0; i.e., the rotational axis 212 lies on the longitudinal axis 208 of the tomographic apparatus. FIGS. 4B and 4C are corresponding reconstructed cross-sectional side view and plan view slices, respectively, of a tomogram of a cylindrical geological core sample for a perfectly aligned system. Because the sample is cylindrical and is rotated about its (vertical) axis of rotational symmetry, the side view or vertical slice of FIG. 4B is rectangular, whereas the plan view or horizontal slice of FIG. 4C is circular. The images are sharp and structural features of the sample are resolved to the spatial resolution of the system for a sample of this composition and geometry.

To illustrate the effects of misalignment on the reconstructed images, FIG. 5A is a schematic illustration of the projection of the rotational axis 212 onto the detector plane 206, where the rotational axis 212 is misaligned or offset from the longitudinal axis 208 of the tomographic apparatus; i.e., Rx>0. For convenience, all misalignments are represented in units of pixels in the projected images. FIGS. 5B and 5C are corresponding reconstructed plan view and cross-sectional side view slices, respectively, of a tomogram of the geological core sample for a misalignment Rx of 2 pixels in the projected images. By comparison with the reconstructed images of FIGS. 4B and 4C from an aligned system, it can be seen that the images from the misaligned system appear blurry, and the spatial resolution of the computed slice images is relatively poor. As expected, this degradation becomes worse with increasing misalignment: FIGS. 5D and 5E are the same as FIGS. 5B and 5C, but for a misalignment Rx of 4 pixels, twice that of FIGS. 5B and 5C.

Similarly, FIGS. 6A to 6E are reconstructed plan view or horizontal slices of a reconstructed tomogram of the cylindrical geological core sample for translational misalignments of the rotational axis 212 of $R_x$=−4, −2, 0, +2, and +4 pixels, respectively. Clearly the quality and sharpness of reconstructed images is highly sensitive to such misalignments, with the image quality highly degraded for misalignments as small as ±2 pixels. In practice, misalignments of ±0.5 pixels are detectable.

Figure 7A:
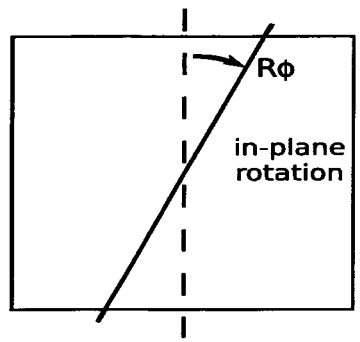
FIG. 7A is a schematic illustration of the projection of a rotationally misaligned rotational axis onto the detector plane of a tomographic imaging apparatus.

Similar effects result from rotational misalignments of the rotational axis 212. FIG. 7A is a schematic illustration of the projection of the rotational axis 212 onto the detector plane 206 where the rotational axis 212 is rotationally misaligned in the detector plane; i.e., Rϕ>0. As indicated in the Figure, for convenience this parameter represents a misalignment rotation of ϕ by the horizontal offset in pixels from the vertical axis at the top of the resulting projected images; i.e., for a square image of N×N pixels, $\phi=\tan^{-1}(2R_\phi/N)$, with ϕ in radians.

Figure 7B:
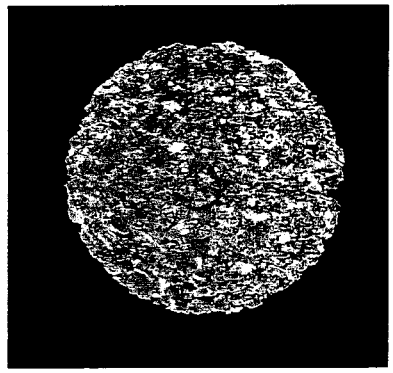
FIGS. 7B and 7C are reconstructed plan view and cross-sectional side view slices, respectively, of a tomogram of the core sample for the rotationally misaligned system of FIG. 7A, where the rotational offset is 2 pixels.
Figure 7C:
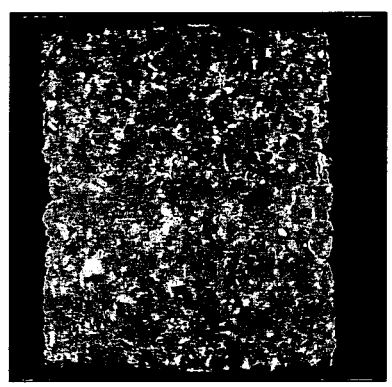
Figure 7D:
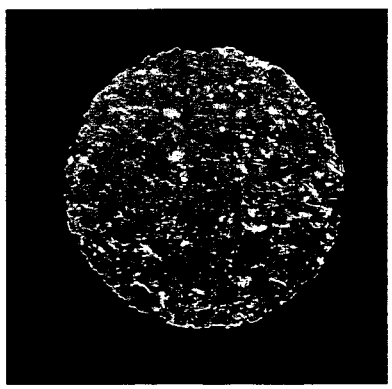
FIGS. 7D and 7E are the same as FIGS. 7B and 7C, but where the rotational offset is 4 pixels.
Figure 7E:
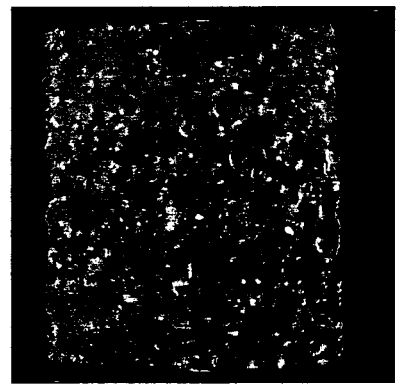

FIGS. 7B and 7C are corresponding reconstructed plan view and cross-sectional side view slices, respectively, of a tomogram of the core sample for the rotationally misaligned system, where the rotational misalignment or offset Rϕ is 2 pixels. FIGS. 7D and 7E are the same as FIGS. 7B and 7C, but where the rotational misalignment Rϕ is 4 pixels. Comparison with FIGS. 4B and 4C confirms that the rotational misalignment degrades the computed images, with the degree of degradation increasing with increasing rotational misalignment. FIG. 6E also illustrates the increasing degradation with distance from the centre of the reconstructed image.

Similarly, FIGS. 8A to 8E are reconstructed side view or vertical slices of reconstructed tomogram of the cylindrical geological core sample for rotational misalignments of the rotational axis 212 of Rϕ=−4, −2, 0, +2, and +4 pixels, respectively. As with the translational misalignments of the rotational axis 212, the quality and sharpness of reconstructed images is sensitive to such misalignments, with the image quality degraded for rotational misalignments as small as ±2 pixels. In practice, misalignments of ±0.5 pixels are detectable.

Figure 9:
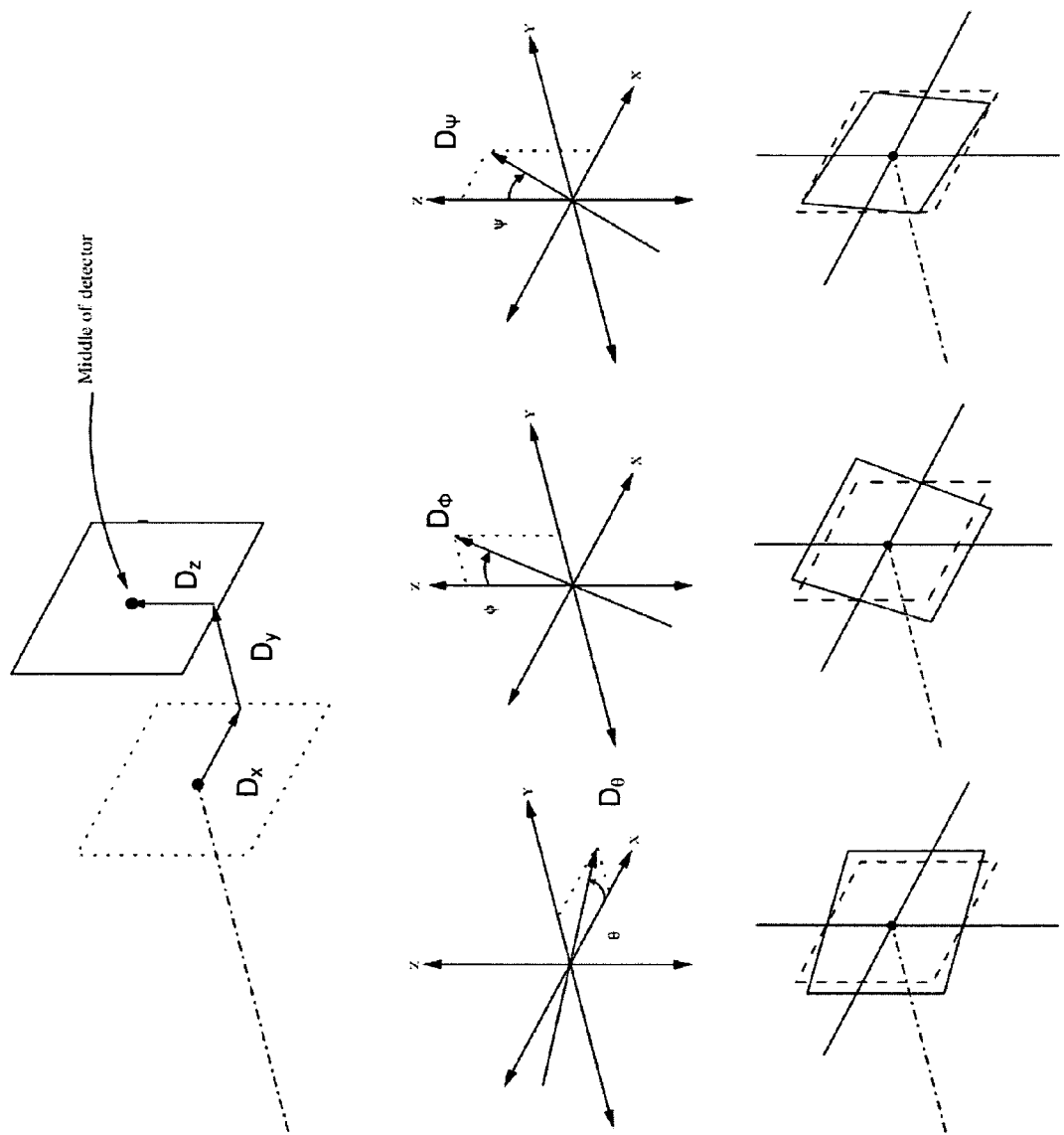
FIG. 9 is a schematic diagram illustrating three forms of detector (angular) misalignment of a tomographic imaging apparatus.

Misalignments of the detector 206 can be represented by three translational misalignment parameters, Dx, Dy (sometimes referred to as ΔCL), and Dz, and three rotational misalignment parameters $D_\theta$, $D_\phi$ and $D_\psi$, the latter corresponding to respective rotational misalignments θ, ϕ, and ψ as shown in FIG. 9. Misalignments of the detector 206 are generally less important because they are not magnified, and the detector 206 can usually be physically aligned with sufficient accuracy. This is true of the rotational misalignments $D_\theta$, $D_\phi$ and $D_\psi$, which are assumed to be zero in the described embodiments because reconstruction is insensitive to these parameters. $D_x$ has the same effect as $R_x$ and consequently is ignored in that a correction nominally for $R_x$ will inherently correct for both $R_x$ and $D_x$. For large CL, the effects of $D_z$ are indistinguishable from those of $R_\psi$, and hence can be ignored.

The only detector alignment parameter used by the described embodiments of the tomographic imaging process is $D_y$, which is important because it determines the cone angle for back-projection. The tomographic imaging process varies $D_y$ together with the rotation axis longitudinal misalignment parameter $R_y$ to maintain a constant magnification value CL/SD. This is important because the magnification determines the number of pixels that correspond to edges in an image and therefore can affect the determined sharpness values without actually affecting the visual sharpness of the image. By maintaining a constant magnification, this problem is avoided.

Figure 10:
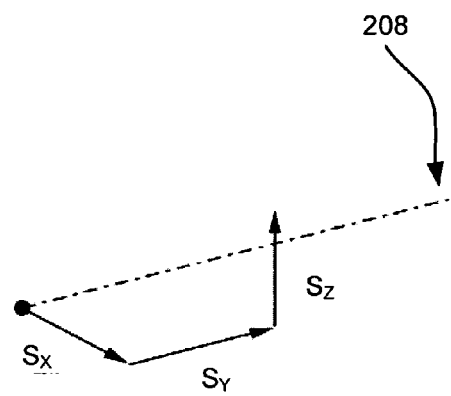
FIG. 10 is a schematic diagram illustrating two forms of source (translational) misalignment of a tomographic imaging apparatus.

The tomographic imaging process represents misalignments of the source 102 by three translational misalignment parameters Sx, Sy, and Sz, as shown in FIG. 10. Accurate knowledge of source position is important because any error is magnified at the detector 106 by CL/SD. For example, a 5 μm translation of the source 102 with a magnification of 20 causes a 100 μm translation of the corresponding projection at the detector 106, which is typically several pixels.

As described above, misalignments of the source 102, rotation axis 104, and/or the detector 106 degrade the quality of reconstructed images. The tomographic imaging processes described herein effectively measure these misalignments by generating reconstructed image slices for a range of values of one or more corresponding misalignment parameters from the alignment parameters described above, and then analysing the resulting reconstructed images to evaluate the quality of each image. The parameter values that provide the highest quality reconstructed images are then considered to represent the actual misalignments, and are applied to correct the projected images for these misalignments.

In the described embodiments, reconstructed image slices for each combination of misalignment parameters are generated from a set of modified projection data (images). Although the source of misalignments may be the x-ray source 102, rotation axis 104, and/or detector 106, as described above, all of these misalignments can be corrected (or simulated) by modifying the projection images to generated modified projection images or "virtual projections". For example, a translation of the source 102 from its assumed position due to thermal drift can be corrected for as a translation of the detector 106 (and hence a translation in the projected images). A unique alignment line is defined as a line that passes through the source 102 and the rotation axis 104, and is perpendicular to the rotation axis 104. The virtual projections are defined in a two-dimensional coordinate system that is perpendicular to the alignment line and having one axis parallel to the rotation axis 104, and whose origin lies on the alignment line. The virtual projections are generated by mapping the measured projection images from their coordinate system that is assumed to be transformed from the ideal detector position and orientation of the virtual projections, according to the misalignment parameters given.

Figure 11:
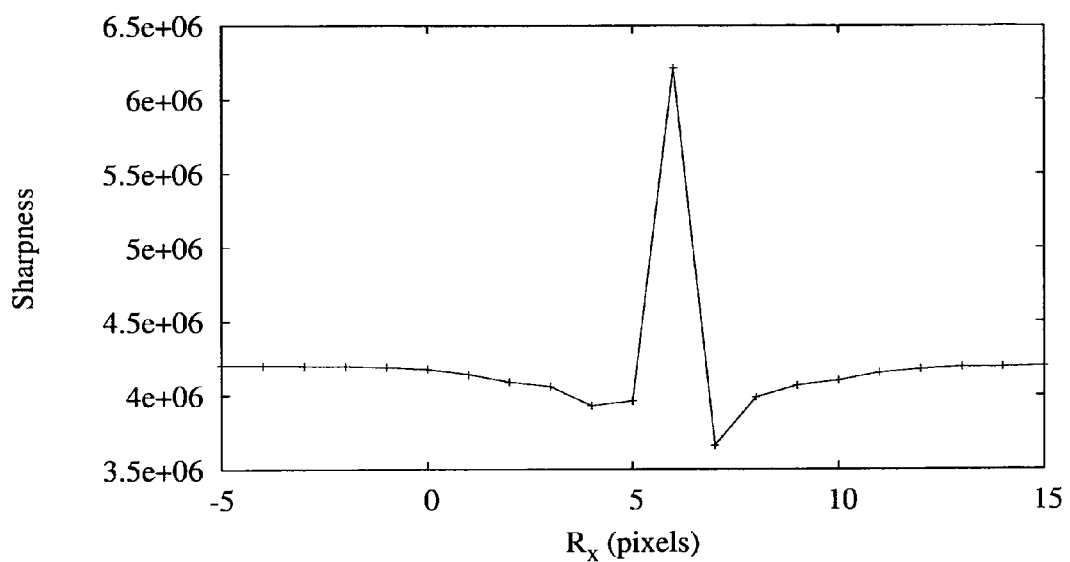
FIG. 11 is a graph of sharpness as a function of translational misalignment.

The quality of reconstructed tomographic images is assessed by evaluating their sharpness, as represented by the magnitudes of the high spatial frequency content of the images. For example, FIG. 11 is a graph of reconstructed image sharpness as a function of Rx, the translational misalignment of the rotational axis 212 from the longitudinal axis 208. That is, a set of projected images was acquired, and subsequently modified by correcting the projected images for each of assumed or trial values of Rx ranging from −5 pixels to +15 pixels. For each of the resulting sets of trial corrected projected images, a reconstructed tomographic image was generated and its quality evaluated using the sharpness equations given above. Clearly, the image sharpness as evaluated in this manner is extremely sensitive to such misalignments, with the sharpness measure increasing by more than 50% at a value of Rx=6 pixels, relative to the adjacent values of Rx=5 and 7 pixels. Because the sharpness and hence quality of the image increases so dramatically for an assumed or trial misalignment of 6 pixels, this value is considered to represent the actual misalignment of the rotational axis 212.

Figure 12:
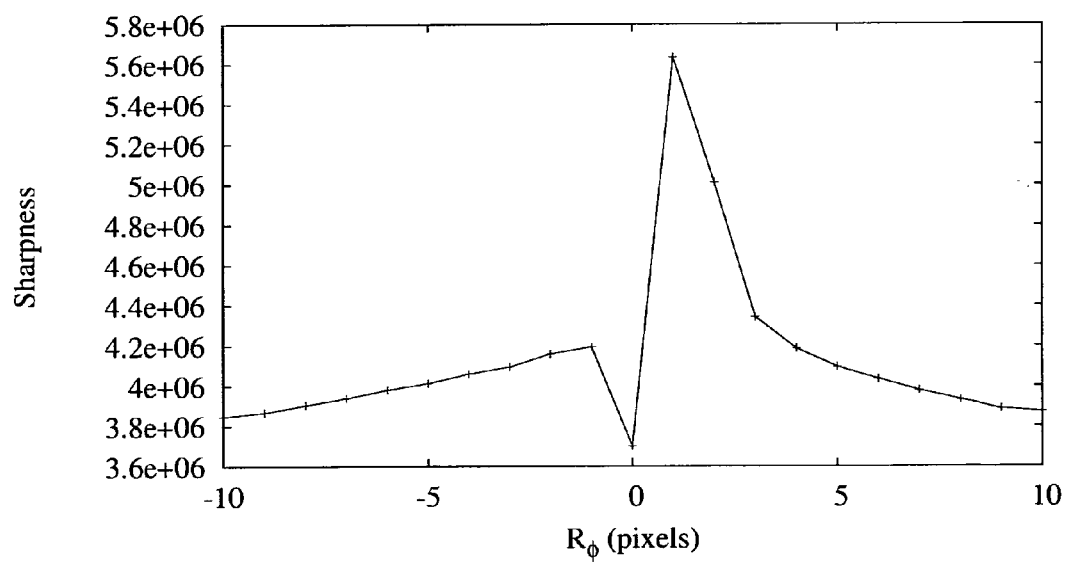
FIG. 12 is a graph of sharpness as a function of rotational misalignment.

Similarly, FIG. 12 is a graph of the reconstructed image sharpness as a function of $R\phi$, the rotational misalignment of the rotational axis 212. Although slightly less well defined that for Rx, the sharpness value at a trial misalignment value of $R\phi=+1$ pixel is substantially and unambiguously higher than at 0 or +2 pixels. The shape of the graph suggests that the true misalignment lies between +1 and +2 pixels.

Figure 13:
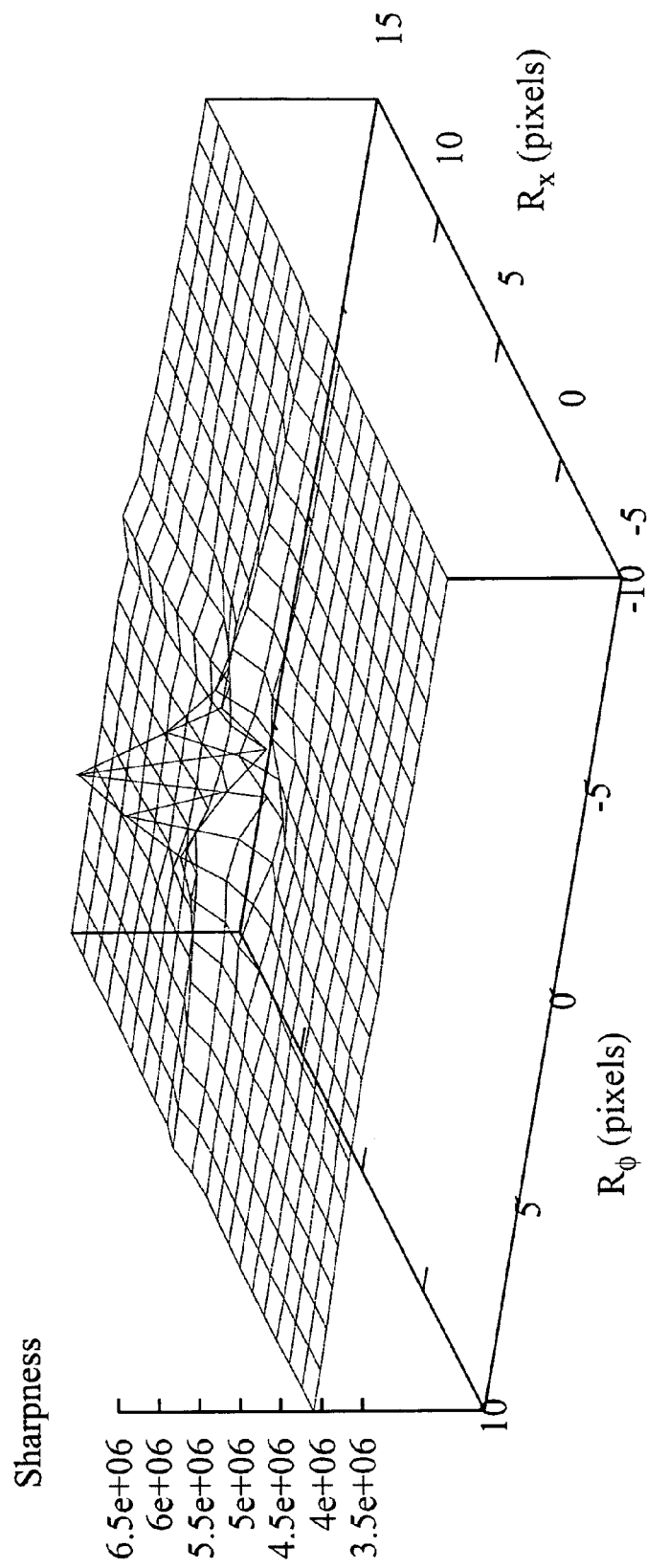
FIG. 13 is a three-dimensional graph of sharpness as a function of translational misalignment and rotational misalignment.

In practice of course, a tomographic imaging apparatus will suffer from multiple simultaneous misalignments. However, the reconstructed image sharpness evaluated as described above is still found to increase substantially when multiple misalignments are simultaneously corrected or compensated. For example, FIG. 13 is a three-dimensional graph of reconstructed image sharpness as a function of both of the misalignment parameters Rx and $R\phi$, showing a sharp peak in the sharpness value when both misalignments are corrected, but no such peak when only one misalignment is corrected. Consequently, the tomographic imaging processes determines the misalignments of a tomographic imaging apparatus by varying relevant misalignment parameters to locate a maximum in the sharpness of the corresponding reconstructed images.

When applied specifically to a CT having a cone-beam geometry, such as that shown in FIG. 1, the misalignment of the system can be defined by seven alignment parameters, as described above. However it has been found that the two detector alignment parameters can be ignored because they have been found to have little effect on image sharpness. Accordingly, the process can be applied to determine only the five most significant alignment parameters.

In practice, varying $R_y$ does not affect the reconstruction geometry, merely the magnification, so the measured value of SD is assumed to be correct. It is varied solely to maintain a constant magnification, CL/SD. As described above, it is important to maintain a constant magnification throughout the parameter searching process, because reconstructions with a higher magnification have a higher sharpness estimate simply because they occupy more of the reconstruction space.

Figure 14:
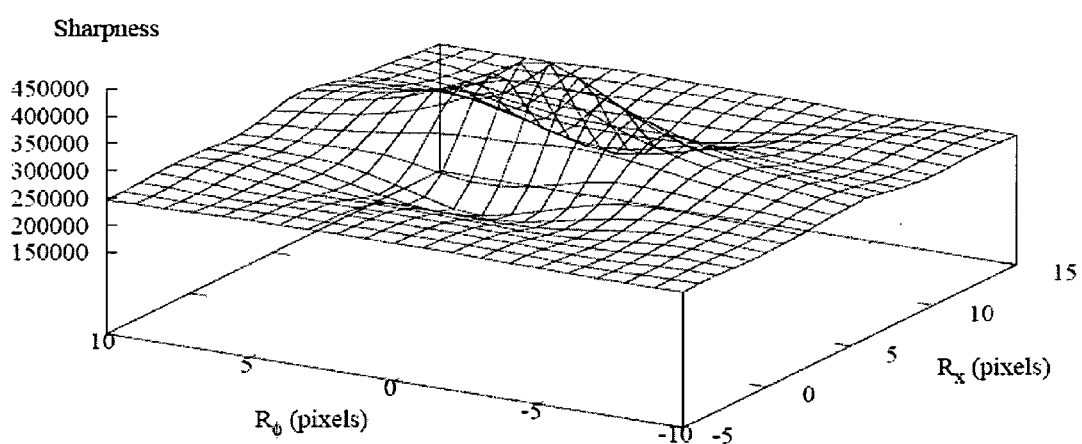
FIG. 14 is the same as FIG. 13, but where the projected images have been blurred, demonstrating that down-sampling projection images leads to good initial estimates of the misalignment information.

The efficiency of this search of misalignment parameter space is improved using the methods described above. Bearing in mind the sharpness of the local maximum in FIG. 13, a gradient-based search to find the maximum may never converge if seeded too far from the optimal parameter values. Accordingly, the two-dimensional projections can be blurred to correspondingly broaden the maximum, making it easier to locate using parameter space scans at low resolution. For example, FIG. 14 is a graph of the same data as shown in FIG. 13, but where the projection images were first blurred using a 15×15 mask. The resulting peak is substantially smoother than the peak in FIG. 13, and is more suitable for use with gradient based optimisation methods, such as Powell's method, for example.

Helical Scanning

A circular scanning tomographic imaging apparatus as described above suffers from a limitation that arises because the set of x-ray projections collected using cone-beam illumination and a circular scan trajectory is not complete: regardless of sampling density, the projection data collected along a circular trajectory does not contain sufficient information for reconstructing the object exactly, with the amount of missing information increasing with distance from the scan trajectory plane. This distance is commonly quantified in terms of the cone-angle, being the largest angle between the trajectory plane and the X-rays hitting the detector 106. It is commonly recognized that the FDK reconstruction algorithm produces reliable results as long as the cone-angle does not exceed 5 degrees. However, this is a significant restriction on the imaging apparatus that limits the effective signal-to-noise-ratio (SNR) of the instrument.

Figure 18:
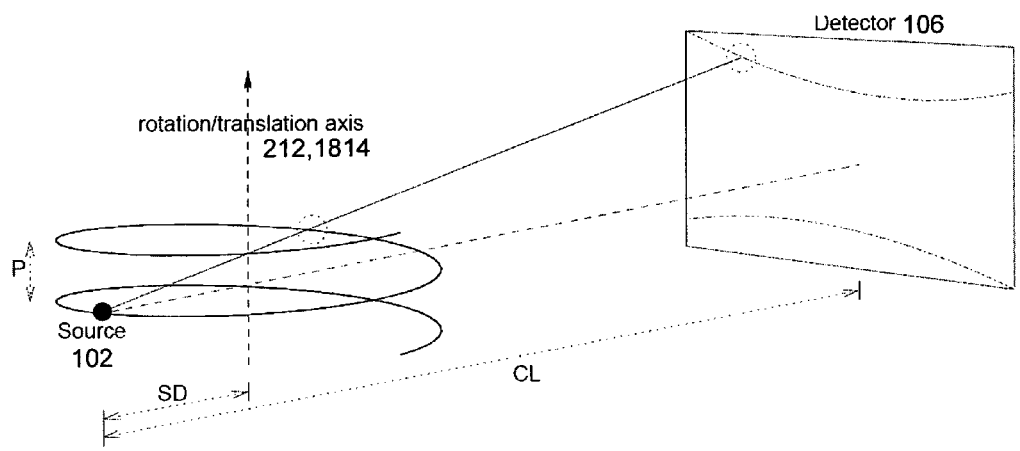
FIGS. 18 and 19 are schematic diagrams illustrating geometric parameters of the helical scanning tomographic imaging apparatus of FIG. 17 in which the approximately vertical translation direction is aligned and misaligned, respectively, with respect to the vertically oriented rotation axis.

To overcome this limitation, other trajectories can be used to collect complete information about the object. For such trajectories, theoretically exact reconstruction methods exist. For example, in the helical scanning tomographic imaging apparatus shown in FIG. 17, the sample stage 104 includes a vertical translation stage as well as a rotation stage as described above, enabling acquisition of data along a helical (or approximately helical) scanning trajectory, as shown in FIG. 18.

The x-ray images of the object or sample 110 are acquired sequentially, with both rotation and translation stages being actuated to rotate and translate the sample by small amounts between successive images, thus providing a series of different geometric projections through the object. As described above, vertical translation and rotation about a vertical axis 212 can be combined to generate a wide range of possible trajectories such that a corresponding series of projections acquired along any one of those trajectories can provide complete information about the object. Such trajectories could include, for example, saddle trajectories and variants of circle-plus-line trajectories, but the embodiment described herein uses a simple helical scanning trajectory. The pitch P of the resulting helical scan path is the amount of vertical movement associated with each complete revolution.

In some embodiments, reconstruction from the helical scan data can be performed exclusively using an inexact method such as the FDK method described above, which has been adapted for helical trajectories (see e.g. G. Wang, T.-H. Lin, and P. C. Cheng *A general cone-beam reconstruction algorithm*, IEEE Transactions in Medical Imaging 12:486-496 (1993)). However, in some embodiments it may be preferable to use a theoretically exact method, either instead of, or in combination with, an inexact method such as FDK. Accordingly, the described helical scanning embodiments also use (at least for the final reconstruction) the theoretically exact filtered back-projection method described in A. Katsevich, *An improved exact filtered backprojection algorithm for spiral computed tomography*, Advances, in Applied Mathematics, 32(4):681-697 (2004). In the described embodiments, the implementation of the Katsevich reconstruction method assumes that the data was collected using a perfectly helical trajectory, where the mid-point of the detector is the closest point to the source (see FIG. 18), and the detector vertical axis (the z-axis) is parallel to the axis of the helix. Deviations from these assumptions result in images of degraded quality.

Figure 19:
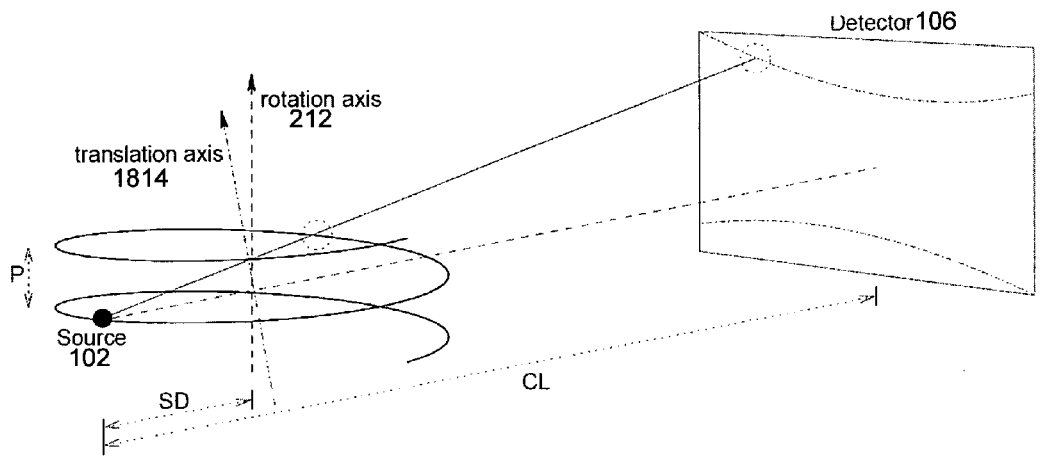

As described above, a circular scanning tomographic imaging apparatus has six misalignments (if sample distance SD is excluded): horizontal and vertical detector offsets ($D_Z$ and $D_x$), the detector in-plane rotation angle $D_\phi$, two out-of-plane detector rotation angles $D_\psi$ and $D_\Theta$, and the camera length CL. Sample distance SD is not included in this list of parameters because it only affects the reconstruction as an isotropic scaling factor for the voxel size. A helical scanning tomographic imaging apparatus requires an additional four misalignment parameters: two angles representing misalignments of the direction of the translation axis 1814 relative to the rotation axis 212 (see the misaligned axes 212, 1814 of FIG. 19), the pitch P, and the sample distance SD. There is, however, some redundancy in this set of 10 parameters. To perform accurate reconstruction from helical scan data, it is necessary to know the camera length CL, the magnification factor CL/SD, and the magnified pitch P×CL/SD. The magnification factor only affects the numerical value of the voxel size in the tomogram, and therefore does not affect the image quality. Any error in the pitch can therefore be scaled out by adjusting the sample distance SD, leaving only an incorrect magnification factor CL/SD that changes scaling but causes no image degradation. This reduces the number of degrees of freedom by one, and means that the measured value for the pitch P can be assumed to be correct. In general, nine alignment parameters are considered for helical scanning.

Figure 20:
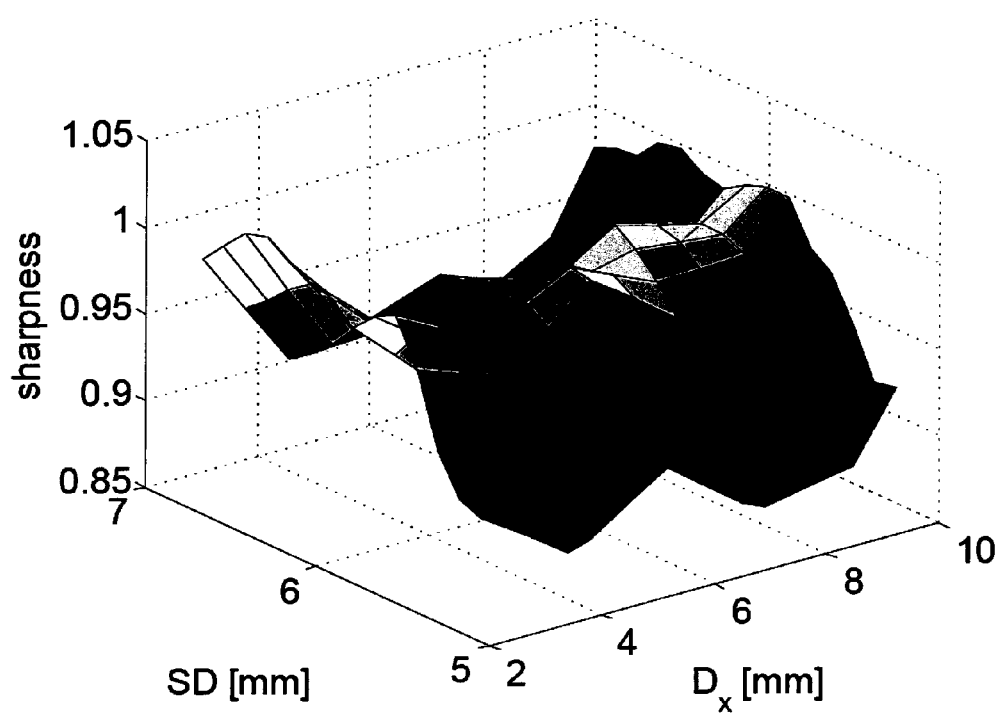
FIGS. 20 and 21 are two-dimensional surface graphs of the sharpness of a reconstructed image as a function of sample distance SD and horizontal detector offset $D_x$ for images generated using Katsevich and FDK reconstruction methods, respectively.

The set of misalignment parameters for a helical scanning tomographic imaging apparatus can be modelled as described above for a circular scanning apparatus, and provided as input to a modified form of the tomographic imaging process described above, together with a corresponding set of two-dimensional projection images. In addition to including the new alignment parameters, the evaluation of the sharpness measure is done differently in the described embodiments of the helical scanning tomographic imaging process because, although the correct misalignment parameters normally constitute a local maximum for the sharpness measure, it is frequently not a global maximum. For example, FIG. 20 is a graph of sharpness as a function of values for the horizontal detector offset $D_x$ and the sample distance SD, using Katsevich reconstruction. Although there is a local maximum for sharpness at the correct location, the sharpness surface has other maxima and which are higher than the correct one. Consequently, optimization based on this function alone will generally not be robust enough for practical use.

As a result, very tight a priori bounds on the alignment parameters are required to ensure that the search will converge to the correct solution using Katsevich reconstruction. This is because the Katsevich reconstruction method uses a minimal set of projection data to reconstruct each point, so that features, depending on their orientation, tend to be shifted rather than blurred, and consequently sharp edges tend to be present also in reconstructions using misaligned projection data.

Figure 21:
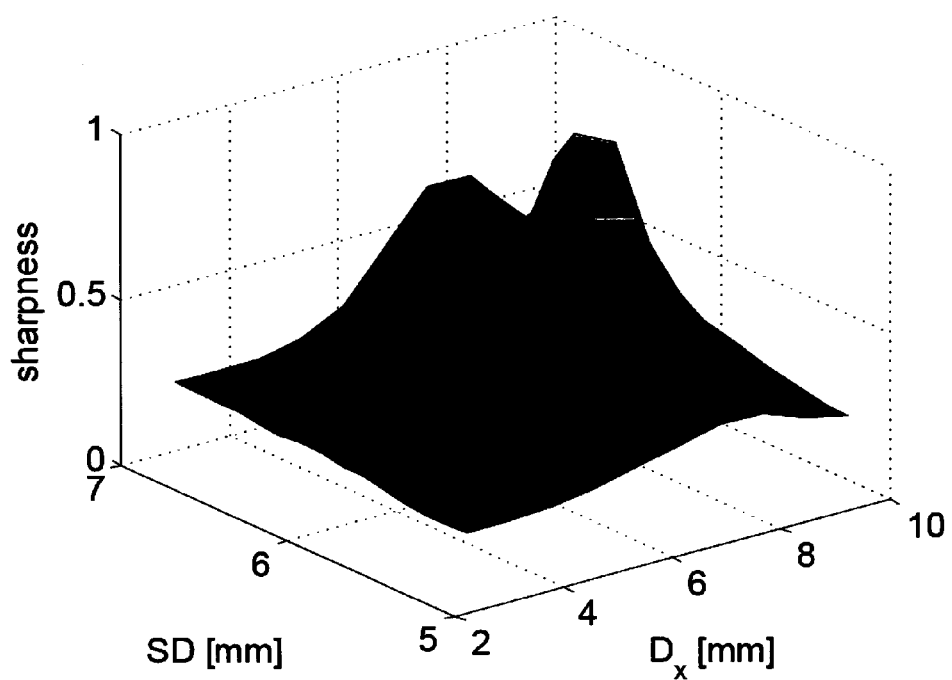

In order to render the search for misalignment parameters sufficiently robust for routine use, the described embodiments use a hybrid approach wherein the robust but non-exact helical FDK method is used to reconstruct the slices needed for sharpness evaluation, and then the Katsevich method is used to obtain the final high quality reconstruction. FIG. 21 is a graph corresponding to that of FIG. 20, but where inexact FDK reconstruction was used. Because the FDK reconstruction tends to generate blurred images for any misalignments (unlike Katsevich reconstruction, compare FIGS. 23 and 24, for example), the resulting surface has a single maximum, it can be used to determine the misalignment parameters for input to the theoretically exact Katsevich reconstruction. Alternatively, the FDK method could be used to determine sufficiently tight bounds on the misalignment parameters that the Katsevich method can be used for a final search of parameter space.

Figure 22:
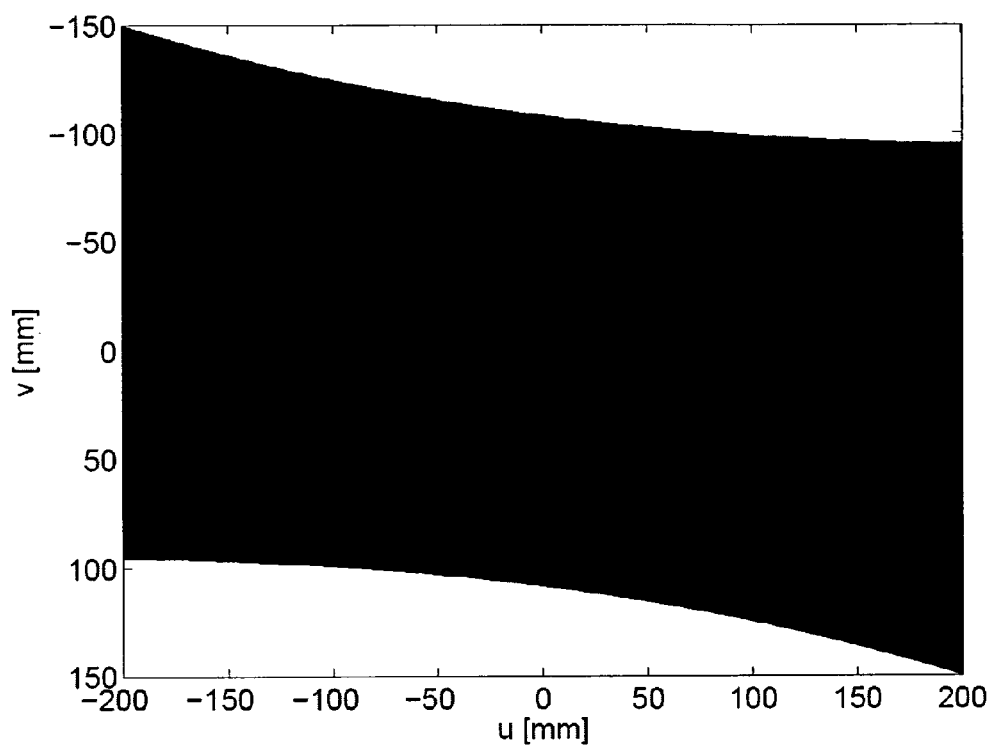
FIG. 22 is a schematic illustration of the (black shaded) region that is back-projected during Katsevich reconstruction.

Since both FDK and Katsevich assume the same basic cone-beam acquisition geometry, the same set of misalignment parameters is used to determine the mapping from projection data to the virtual projections. However, the FDK method uses the entire projection data, whereas the Katsevich method uses a subregion, as shown in FIG. 22. This additional (redundant) projection data means that while the FDK method generates imperfect reconstructed images, it reliably produces the sharpest images when the virtual projections are aligned. Because FDK reconstruction is less computationally demanding than Katsevich reconstruction, the hybrid approach is also beneficial from a computational point of view.

CONCLUSION

The tomographic imaging processes described herein thus automatically determine the best alignment parameters that map each projection image from an experimental detector plane onto a virtual detector plane that adheres to the strict geometrical requirements assumed by tomographic reconstruction methods.

Hardware alignment or even physical measurement of alignment parameters can be insufficient because the required alignment precision can be below what is physically possible (as is currently the case for nanoscale CT) and/or there can be motion during an experiment such as source drift due to temperature variation, for example.

Therefore an automated process that, given an alignment model, can automatically determine (in a reasonable time) the optimal alignment parameters that give the sharpest tomogram is highly advantageous.

Moreover, the processes described herein determine misalignments from projection images of a sample or object of interest and apply those determined values to the same data set.

The processes are completely automated and provide a stable, robust and autonomous solution to the problem of blurry 3D tomographic images that result from projection images collected with imperfect and/or unknown geometric alignments between the various components of tomographic instruments.

The described alignment processes can be applied to any tomographic data (even retrospectively on archived data previously thought unusable) without any information except an appropriate model to parameterise alignment, provided that the misalignments result in a reduction in sharpness of the reconstructed image. The processes can be applied to cone or parallel beam tomography with circular, helical, or other scanning trajectories. Given no model for source-sample movement, the processes will find the best average alignment parameters.

Any type of alignment parameters can be incorporated and corrected simply by developing an appropriate correction model and identifying these parameters. For example, misalignments for parallel scan geometries and/or for time-dependent misalignments, such as thermal drift of various components.

Figure 15:
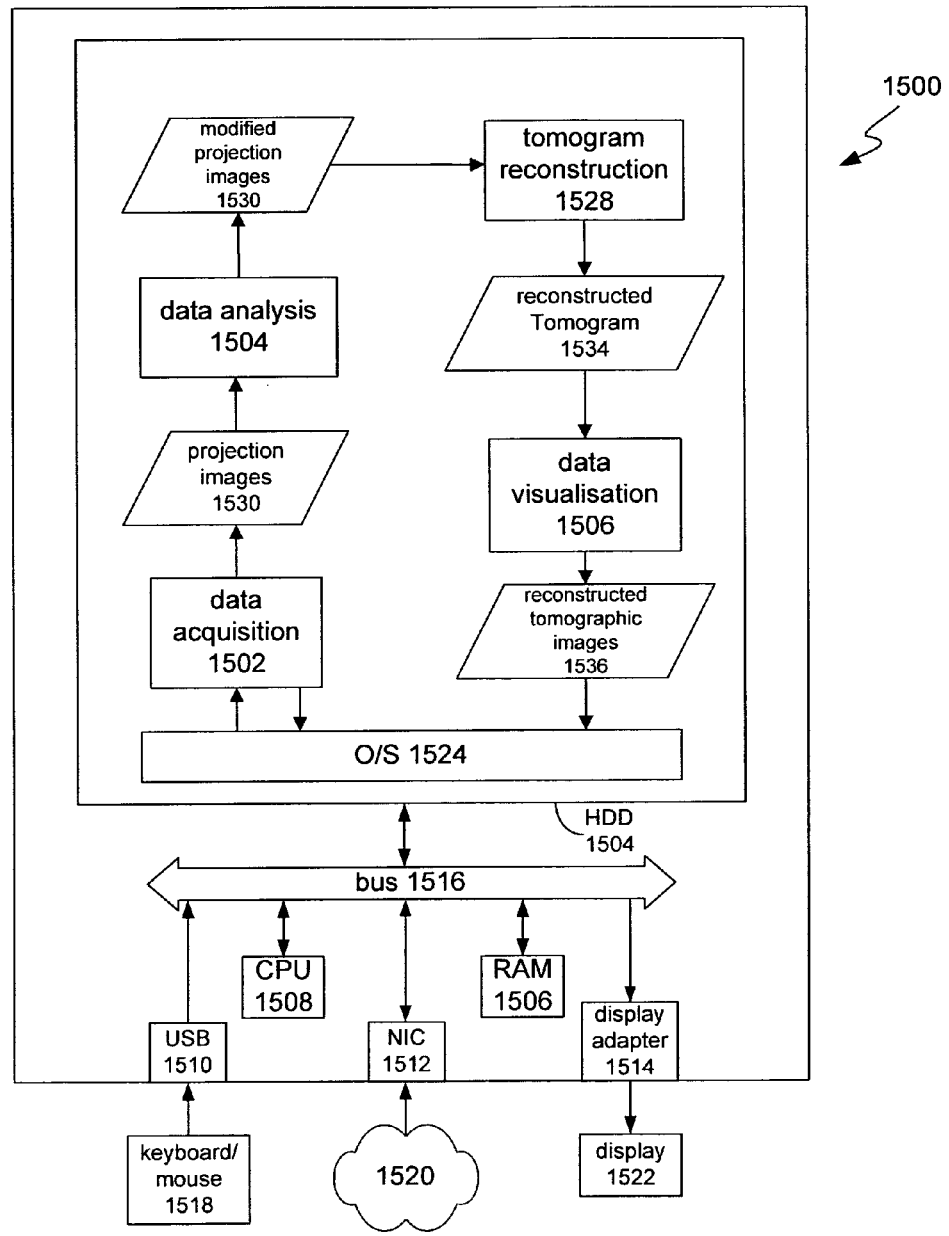
FIG. 15 is a block diagram of an embodiment of a computed tomography imaging system.

As will be appreciated by those skilled in the art, the tomographic imaging processes described herein can be embodied in a variety of different forms, but may be most conveniently embodied in the form of computer-executable programming instructions of one or more software modules. Accordingly, in the described embodiments, the tomographic imaging apparatus includes a standard computer system 1500 such as an Intel IA-32 or IA-64 based computer system, as shown in FIG. 15, and the tomographic imaging process is executed by the computer system 1500 and is implemented as programming instructions of one or more software modules 1502 stored on non-volatile (e.g., hard disk or solid-state drive) storage 1504 associated with the computer system 1500. However, it will be apparent that at least parts of the tomographic imaging process could alternatively be implemented as one or more dedicated hardware components, such as application-specific integrated circuits (ASICs) and/or field programmable gate arrays (FPGAs), for example.

The computer system 1500 includes standard computer components, including random access memory (RAM) 1506, at least one processor 1508, and external interfaces 1510, 1512, 1514, all interconnected by a bus 1516. The external interfaces include universal serial bus (USB) interfaces 1510, at least one of which is connected to a keyboard 1518 and a pointing device such as a mouse 1519, a network interface connector (NIC) 1512 which connects the system 1500 to a communications network such as the Internet 1520, and a display adapter 1514, which is connected to a display device such as an LCD panel display 1522 for viewing the tomographic images.

Figure 16:
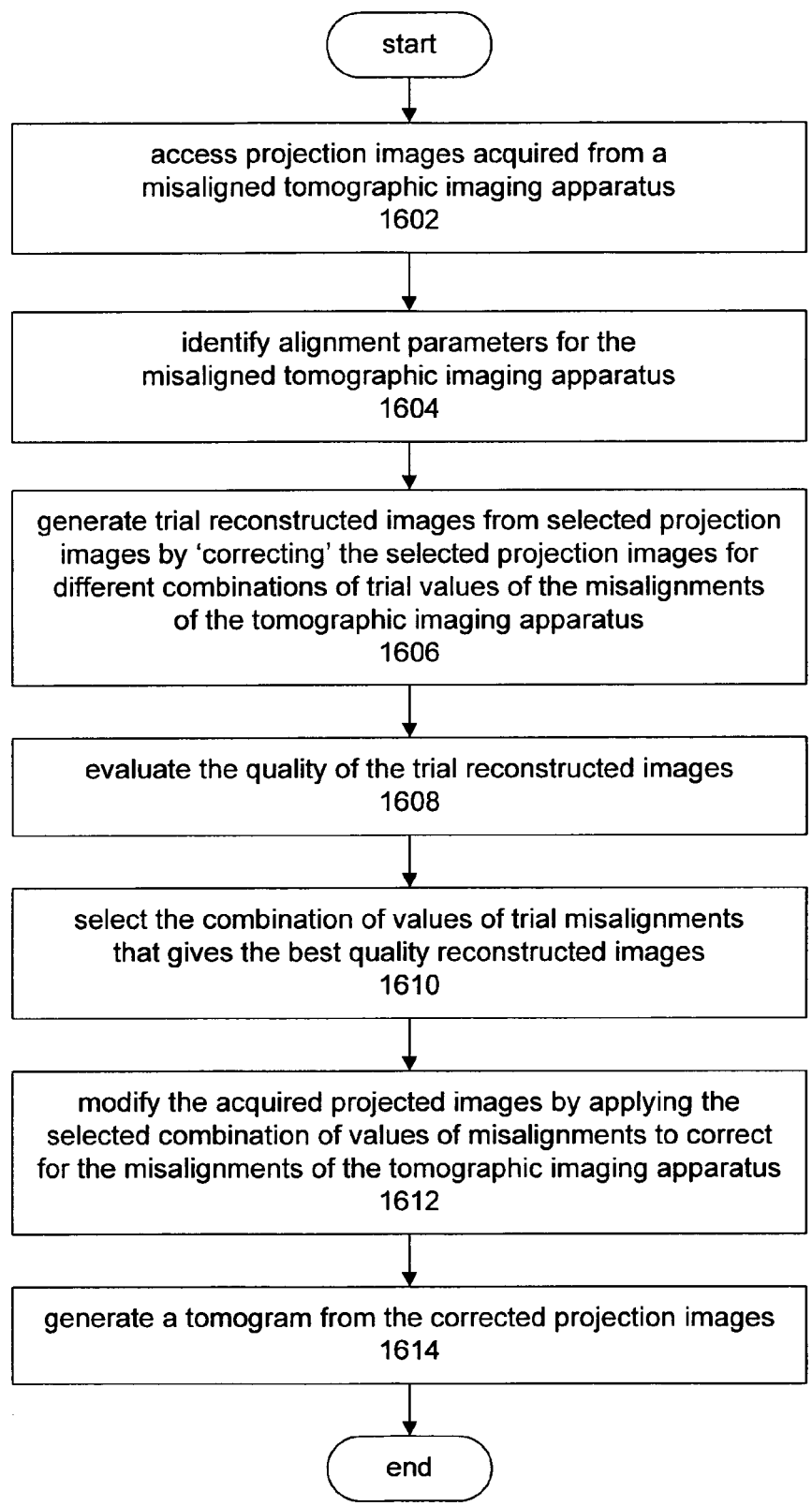
FIG. 16 is a flow diagram of an embodiment of a computed tomography imaging process of the tomographic imaging system.

The system 1500 also includes a number of other software modules 1524 to 1530, including an operating system 1524 such as Linux, Apple Inc.'s OS X, or Microsoft Windows, a data acquisition module 1526, a tomogram reconstruction module 1528, and a data visualisation module 1530. The data acquisition module 1526 controls the rotation stage 212, receives data from the detector 106, and stores the received data as the projection images 1530. The data analysis module 1502 performs the tomographic imaging process shown in FIG. 16 to determine the values for misalignment parameters of the imaging components 102, 104, 106 of the system, thereby to generate corrected projection images 1532. The reconstruction module 1528 processes the corrected projection images 1532 to generate a tomogram 1534. Finally, the data visualisation module 1530 processes the tomogram 1534 to generate reconstructed tomographic images 1536 in real-time under user control.

Many modifications will be apparent to those skilled in the art without departing from the scope of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLE I

Circular Scanning

The tomographic imaging process described above was applied to the tomographic imaging apparatus shown in FIG. 1. The apparatus is a cone-beam micro-CT and used a circular trajectory and the standard FDK method for reconstruction, as described above. The x-ray source 102 is fixed and the sample stage 104 and detector 106 are mounted on a set of rails and can be translated arbitrarily up to 2 m. The source spot size is 3-5 micron in diameter and the CCD detector has $2048^3$ square pixels of size 24 micron. The alignment parameters can vary between each experiment because the rails are not exactly parallel or straight, and moving the sample stage 104 or detector 106 changes the geometry. The parameters can also vary within a single experiment, because the source position can drift with temperature (as described above), and the sample may move.

The misalignment parameters for this system were modelled as described above and provided as input to the tomographic imaging process, together with a set of two-dimensional projections images of a geological core sample, as described above. In this example, the tomographic imaging process used a brute force search of parameter space with the efficiency improvements described above.

The tomographic imaging process determined values for the four misalignment parameters $R_x$, $R_\phi$, $R_\psi$, and $D_y$, using a partially iterative process with six parameter scans, as summarised in the Table below. The first and second scans were performed on low resolution versions of the projection images, at a resolution of 512×512 pixels. The first scan varied only the $R_x$ parameter from −64 to +64 in steps of +4 pixels, and only a single slice of the tomogram was generated. Having obtained a low-resolution estimate for Rx, the second scan varied the two rotational misalignment parameters $R_\phi$ and $R_\psi$, each being varied from −10 to +10 pixels in steps of 2 pixels, with the $R_x$ parameter being held at the value determined by the first scan. Three (transverse (t), coronal (c), and saggital (s)) mutually orthogonal slices of the tomogram were generated at pixel values of 512, 1024, and 1536.

| scan | scale | $R_x$ search | $R_\phi$ search | $R_\psi$ search | $D_y$ search | slices |
|---|---|---|---|---|---|---|
| 1 | 512 | −64:64:4 | — | — | — | t: 1024 |
| | | | | | | c: — |
| | | | | | | s: — |
| 2 | 512 | — | −10:10:2 | −10:10:2 | — | t: 512, 1024, 1536 |
| | | | | | | c: 512, 1024, 1536 |
| | | | | | | s: 512, 1024, 1536 |

-continued

| scan | scale | $R_x$ search | $R_\phi$ search | $R_\psi$ search | $D_y$ search | slices |
|---|---|---|---|---|---|---|
| 3 | 1024 | −3, 3, 1 | −3, 3, 1 | — | — | t: —<br>c: 512, 1024, 1536<br>s: 512, 1024, 1536 |
| 4 | 1024 | — | — | −4, 4, 2 | −8, 8, 2 | c: 512, 1024, 1536<br>s: 512, 1024, 1536 |
| 5 | 2048 | −1.5, 1.5, 0.5 | −1.5, 1.5, 0.5 | — | — | t: —<br>c: 511, 853, 1195, 1537<br>s: — |
| 6 | 2048 | — | — | −2, 2, 1 | −3, 3, 1 | t: —<br>c: 511, 853, 1195, 1537<br>s: — |

Using the value of $R_\psi$ estimated by the second scan, the third scan varied Rx and $R_\psi$, only, each being varied from −3 to +3 pixels about the estimated values determined by scans 1 and 2, respectively, in steps of 1 pixel, and operating on projection images scaled down to 1024×1024 and hence a tomogram scaled down to $1024^3$. Using the resulting estimates for Rx and $R_\phi$, the fourth scan only varied the parameters $R_\psi$ and $D_y$, each being varied in steps of 2 pixels. $D_y$ was varied from −8 to +8 pixels, but since an estimate for $R_\psi$ had already been obtained from the second scan, it was only varied between −4 and +4 pixels about the estimated value determined by scan 3.

The final two scans were performed on full resolution 2048×2048 projection images. The first varied Rx and $R_\phi$ from −1.5 to +1.5 pixels in steps of 0.5 pixels about the previously estimated values to determine final values for these two misalignment parameters. The final scan was of $R_\psi$ and $D_y$, these being respectively varied from −2 to +2 and −3 to +3, respectively, in steps of 1 pixel about the previously estimated values. The resulting values for $R_x$, $R_\phi$, $R_\psi$, and $D_y$ determined in this manner are then applied to the entire set of projection images to correct these misalignments by applying corresponding translation, rotation, and/or scaling operations to the images. The standard FDK reconstruction procedure was then applied to the corrected projection images to obtain a tomogram of substantially higher quality than a tomogram generated from the uncorrected projection images.

The six scan steps, scan ranges and step sizes described above have been found in practice to efficiently provide accurate results for the tomographic imaging apparatus described herein. In general, the optimisation parameters can be found by trial and error and the scan ranges can be estimated based on the measured alignment accuracy of the particular tomographic imaging apparatus used to acquire the projection images. More generally, a generalised optimisation algorithm can be applied to the data without a priori knowledge of these parameters.

EXAMPLE II

Helical Scanning

The helical scanning tomographic imaging process described above was applied to the tomographic imaging apparatus shown in FIG. 17.

Note that, unlike the previous example, the out-of-plane detector tilts $D_\psi$ and $D_\theta$ were included as possible misalignments in this example, because sensitivity to these parameters is higher at increased cone-angles. On the other hand, the vertical translation axis was assumed to be perfectly aligned with the rotation axis. This means that the mapping which takes projections onto aligned virtual projections is the same for every projection, and reduces the number of alignment parameters from nine to seven.

As in the circular scanning example described above, in this helical scanning example the tomographic imaging process used a brute force search of parameter space, albeit with some efficiency improvements. A reasonable search for all seven alignment parameters is not feasible if the full tomogram is to be reconstructed for each evaluation of the sharpness; therefore, a few representative slices were selected to reconstruct, and the sharpness of only these slices was evaluated, rather than the full reconstruction. Additionally, the initial searches were performed at coarser scales, with sub-sampled projection data, as described above. These efficiency improvements are described in more detail below.

As for circular scans, the misalignment parameters for helical scans affect the reconstruction in different ways and it is possible to take advantage of this to optimise the search algorithm. Indeed, there is a preferred search order for which the parameters sequentially decouple, in the sense that a parameter can be found using a one-dimensional parameter search, then using the best candidate for this parameter when proceeding to search for the next parameter using a one-dimensional search. The initial guess for all parameters is that the hardware adheres to the ideal helix acquisition geometry, and the initial one-dimensional search is performed over the whole range of the uncertainty in each parameter. Searches at higher resolutions are only performed in a small range about the previous parameter estimate, thereby limiting the number of reconstructions that need to be performed at high resolution. The search order, as well as the preferred slices to reconstruct when evaluating the sharpness for each parameter is as follows:

1. Horizontal detector offset $D_x$: three horizontal slices.
2. Sample distance SD: two orthogonal vertical slices. In order to reconstruct the same features, the height of the slice is scaled with the relevant magnification change CL/SD
3. In-plane detector rotation $D_\phi$: two vertical slices.
4. Vertical detector offset $D_z$: six slices, consisting of two sets of three orthogonal slices.
5. Out-of-plane detector tilt $D_\theta$: three horizontal slices.
6. Camera length CL: six slices; two sets of three orthogonal slices. SD is scaled commensurately so that image magnification is kept constant.
7. Out-of-plane detector tilt $D_\psi$: three horizontal slices.

It is convenient to measure misalignments in terms of units referred to herein as optimal units. For each parameter, one optimal unit is defined as that misalignment which results in the projection of a point in the object being displaced by a maximum of one pixel at the detector at full resolution. Consequently, a misalignment of 0.5 optimal units results in ray displacements in the range [−0.5,+0.5] pixels, leading to relative displacements up to one pixel. Misalignments less than 0.5 optimal units should therefore be unnoticeable in the reconstruction result. For example, the optimal unit for $D_x$ is simply one detector pixel, while optimal units for other parameters are more complicated and can be determined from the system geometry.

In this example, the searching was performed by making three passes through the 7-stages described above. In the first pass, the data was downsampled by a factor of 4 to 512, and the a search range of −40 to 40 optimal units in steps of 4 was used for $R_x$, followed by a search of −40 to 40 optimal units in steps of 4 for SD. The system was sufficiently well aligned that no search was performed at this resolution for the other 5 misalignment parameters.

For pass 2 with a downsample factor of 2, the search range was −6 to 6 optimal units with a step size of 2 for all 7 misalignment parameters.

For the final pass at full resolution, the search range was −2 to +2 optimal units with a step size of 1.

At each stage, quadratic interpolation is used to estimate the value for each misalignment parameter from the evaluations.

Figure 23:
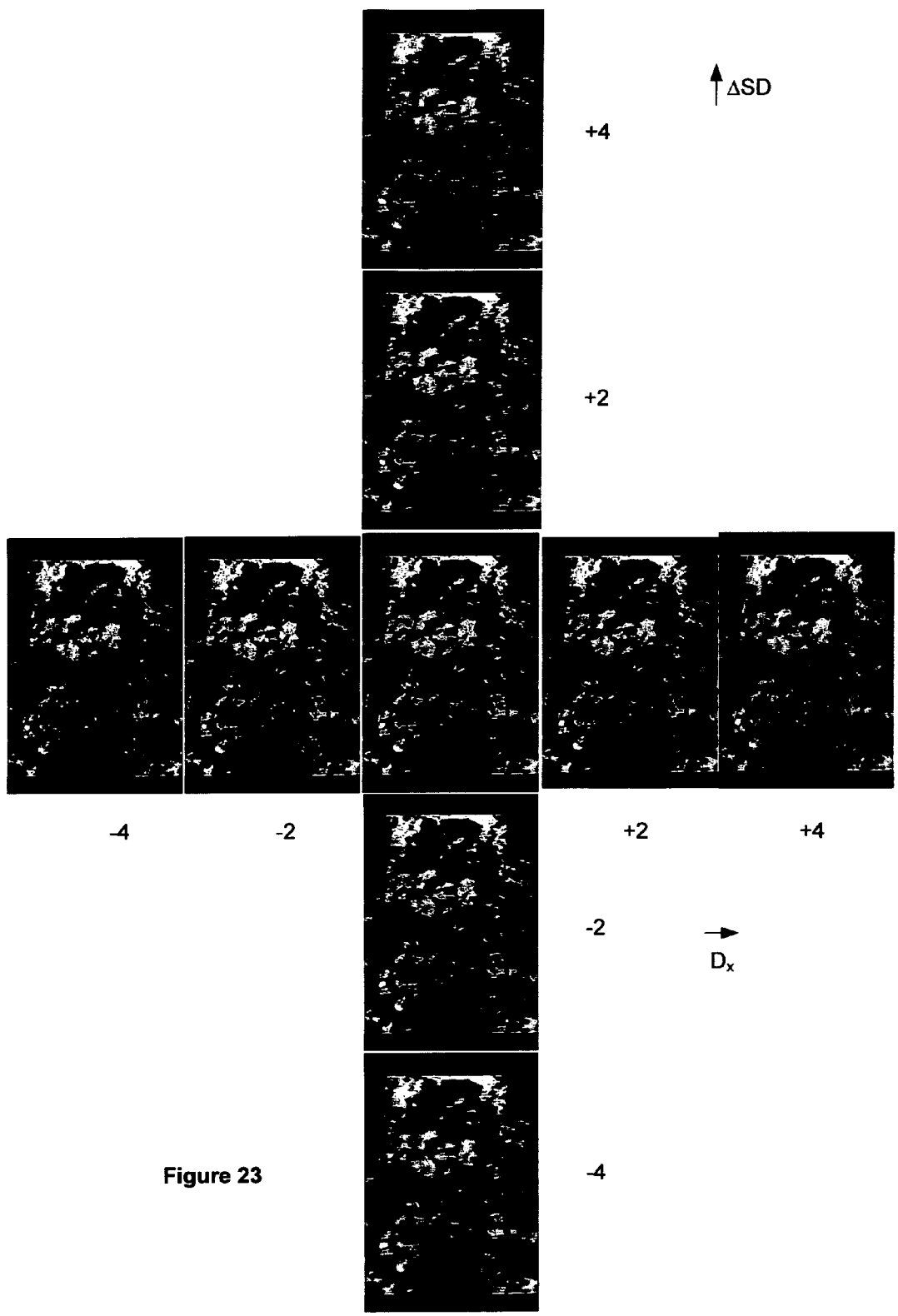
FIG. 23 includes sets of reconstructed images generated using FDK reconstruction for misalignments of the horizontal detector offset $D_x$ (horizontal direction) and sample distance $\Delta SD$ (vertical direction) of −4, −2, 0, +2, and +4 optimal units.

Examples of the resulting reconstructed images of vertical slices through the sample are shown in FIG. 23 for FDK reconstruction and misalignments of −4, −2, 0, +2, and +4 optimal units for each of the two alignment parameters $D_x$ (the horizontal detector offset) and the sample distance offset ΔSD. As expected, the image with no offset in either parameter (i.e., perfect alignment) is the clearest.

Figure 24:
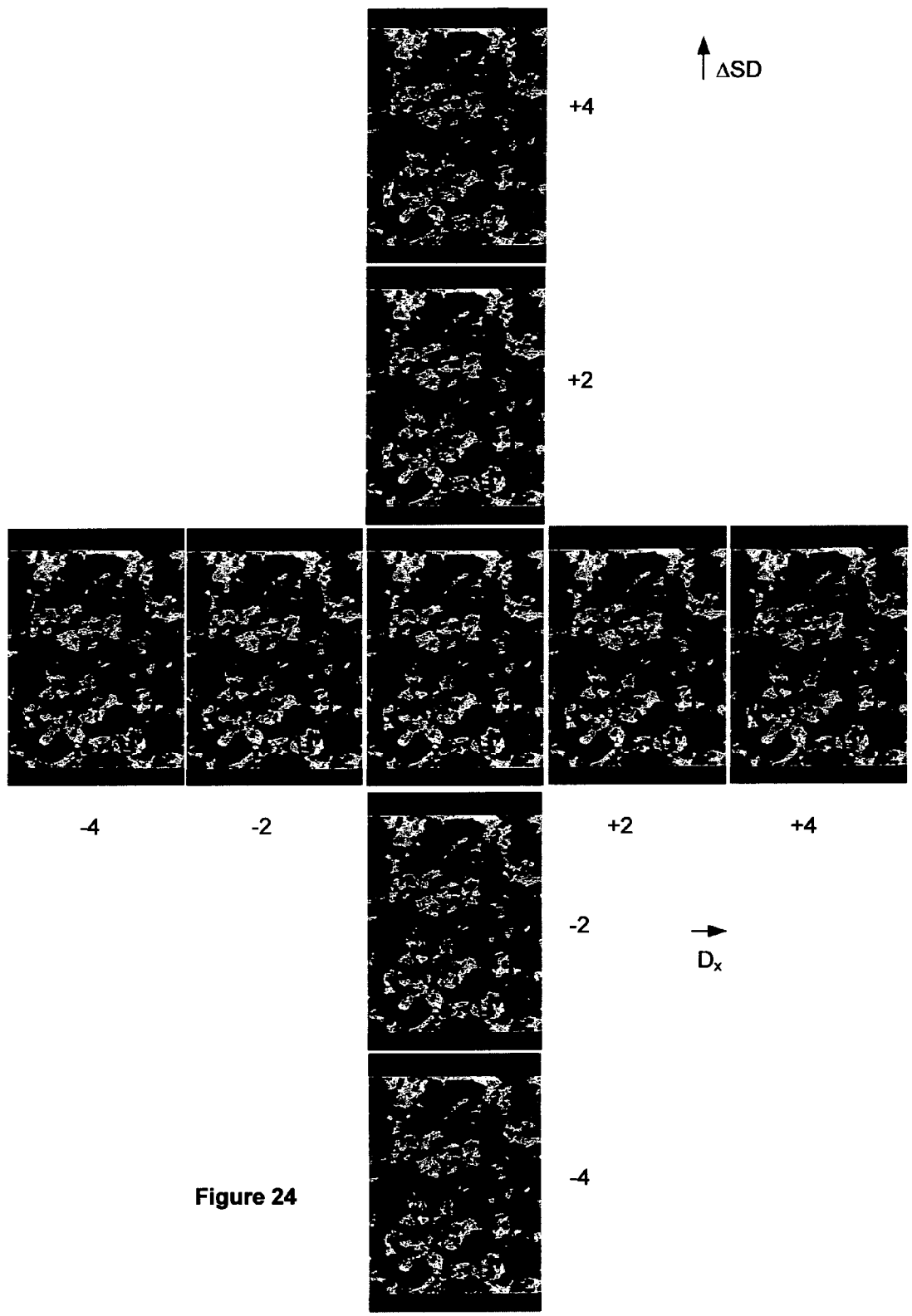
FIG. 24 is the same as FIG. 23, but where the reconstructed images are generated using a theoretically exact Katsevich reconstruction; from a comparison with FIG. 23, it is apparent that the Katsevich reconstructed images remain fairly sharp even when the apparatus is misaligned.

For comparison, FIG. 24 is the same as FIG. 23, but using Katsevich reconstruction, rather than FDK. It is apparent from a comparison with the images of FIG. 23 that Katsevich reconstruction does not tend to produce blurred images as readily as FDK, and consequently is not as effective at identifying the correct alignment when image sharpness is used to assess the quality of the reconstructed images over a wide range of misalignment parameters. However, the Katsevich reconstruction is theoretically exact and provides the most accurate reconstructed images once the misalignments have been determined and corrected.

The invention claimed is:

1. A computed tomography imaging process, including:
accessing projection data representing two-dimensional projection images of an object acquired using a misaligned tomographic imaging apparatus; and
processing the projection data to generate misalignment data representing one or more values that quantify respective misalignments of the tomographic imaging apparatus, wherein processing of the projection data includes processing the projection data to generate trial reconstructed tomographic cross-sectional images for each of a plurality of different slices of the corresponding tomogram.

2. The process of claim 1, including processing the projection data in accordance with the misalignment data to generate a tomogram of the object in which the one or more misalignments of the tomographic imaging apparatus have been substantially corrected.

3. The process of claim 1, including processing the projection data in accordance with the misalignment data to generate modified projection data representing projection images of the object in which the one or more misalignments of the tomographic imaging apparatus have been substantially corrected.

4. The process of claim 1, wherein the projection data is acquired along a scanning trajectory involving rotation of the object about a rotation axis, and the processing of the projection data includes processing the projection data to generate at least one trial reconstructed tomographic cross-sectional image that is not orthogonal to the rotation axis.

5. The process of claim 1, wherein the slices represent orthogonal spatial orientations.

6. The process of claim 1, wherein the slices represent all three orthogonal spatial orientations.

7. The process of claim 1, wherein each misalignment value is determined by selecting one of the trial values of the misalignment that provides the best quality, or by interpolation based on the trial values and the corresponding evaluations of quality.

8. The process of claim 1, wherein the values that best estimate each misalignment are determined iteratively, with the iterations terminating when the values have been determined to an accuracy of less than 0.5 voxels.

9. The process of claim 1, wherein the two-dimensional projection images of the object are acquired along a scanning trajectory produced by combining rotation and translation such that the two-dimensional projection images represent complete information about the object.

10. The process of claim 9, wherein the scanning trajectory is helical or approximately helical.

11. A non-transitory computer-readable medium having stored thereon computer-executable instructions configured for execution of the process of claim 1.

12. A computed tomography imaging system configured to execute the process of claim 1.

13. A computed tomography imaging process, including:
accessing projection data representing two-dimensional projection images of an object acquired using a misaligned tomographic imaging apparatus; and
processing the projection data to generate misalignment data representing one or more values that quantify respective misalignments of the tomographic imaging apparatus wherein the processing of the projection data includes:
processing the projection data to generate trial reconstructed tomographic cross-sectional images for respective trial values of at least one misalignment of the tomographic imaging apparatus;
processing the trial reconstructed tomographic images to generate respective evaluations of quality of the trial reconstructed tomographic images; and
for each said at least one misalignment of the tomographic imaging apparatus, determining a corresponding value that best estimates the misalignment, based on the trial values and the corresponding evaluations of quality.

14. The process of claim 13, wherein the trial reconstructed tomographic cross-sectional images are generated by using fixed spatial positions and orientations for a source and rotation axis of the tomographic imaging apparatus and modifying the projection images to simulate the effect of changing the spatial position and/or orientation of a detector of the tomographic imaging apparatus.

15. A computed tomography imaging process, including:
accessing projection data representing two-dimensional projection images of an object acquired using a misaligned tomographic imaging apparatus; and
processing the projection data to generate misalignment data representing one or more values that quantify respective misalignments of the tomographic imaging apparatus wherein the processing of the projection data includes evaluating the quality of reconstructed tomographic cross-section images generated on the basis of different combinations of values of said misalignments, and selecting one of said combinations based on said evaluations.

16. The process of claim 15, wherein the selected combination is the combination that gives the highest quality reconstructed tomographic image.

17. The process of claim 15, wherein the quality of reconstructed tomographic images is evaluated using spatial information of the reconstructed tomographic images.

18. The process of claim 17, wherein the spatial information is evaluated by evaluating a measure of sharpness of the reconstructed tomographic images.

19. The process of claim 18, wherein the sharpness of each reconstructed tomographic image is evaluated using the magnitudes of values in the image processed by a differentiation filter, or the magnitudes of high frequency transform coefficients generated by applying a mathematical transform to the image.

20. The process of claim 15, wherein the misalignment value combinations are chosen to maintain a constant magnification.

21. The process of claim 15, wherein an initial estimate for each misalignment is obtained by scanning parameter space at a lower spatial resolution using down-sampled projection images, and progressively higher resolution images are then used to refine the estimates until a final full-resolution estimate is obtained.

22. A computed tomography imaging process, including:
accessing projection data representing two-dimensional projection images of an object acquired using a misaligned tomographic imaging apparatus; and
processing the projection data to generate misalignment data representing one or more values that quantify respective misalignments of the tomographic imaging apparatus wherein the processing of the projection data to generate the misalignment data includes using a first reconstruction method to generate reconstructed images whose quality is assessed to determine misalignments of the tomographic imaging apparatus, and the process includes using a second reconstruction method to generate a tomogram of the object in which the one or more misalignments of the tomographic imaging apparatus have been substantially corrected.

23. The process of claim 22, wherein the first reconstruction method uses redundant projection data that is not used in the second reconstruction method.

24. The process of claim 22, wherein the processing of the projection data to generate the misalignment data includes using the first reconstruction method to determine approximate values for the misalignments of the tomographic imaging apparatus, and using the second reconstruction method to determine accurate values of those misalignments.

25. The process of claim 22, wherein the second reconstruction method is a theoretically exact filtered-back-projection reconstruction method.

26. The process of claim 22, wherein the first reconstruction method is based on Feldkamp-Davis-Kress reconstruction.

27. A computed tomography imaging system, including a data analysis component configured to:
receive projection data representing two-dimensional projection images of an object acquired using a misaligned tomographic imaging apparatus;
process the projection data to generate misalignment data representing one or more values that quantify respective misalignments of the tomographic imaging apparatus; and
process the projection data in accordance with the misalignment data to generate modified projection data representing projection images of the object in which the one or more misalignments of the tomographic imaging apparatus have been substantially corrected; wherein the processing of the projection data includes processing the projection data to generate trial reconstructed tomographic cross-sectional images for each of a plurality of different slices of the corresponding tomogram.

28. The system of claim 27, wherein the processing of the projection data includes evaluating the quality of reconstructed tomographic cross-section images generated on the basis of different combinations of values of said misalignments, and selecting one of said combinations based on said evaluations.

29. The system of claim 28, wherein the quality of reconstructed tomographic images is evaluated using spatial information of the reconstructed tomographic images.

* * * * *